(12) United States Patent
Jones et al.

(10) Patent No.: US 7,115,609 B2
(45) Date of Patent: Oct. 3, 2006

(54) ALANYL-PIPERIDINE HETEROCYCLIC DERIVATIVES USEFUL AGAINST CARDIOVASCULAR DISEASES

(75) Inventors: Stuart Donald Jones, Macclesfield (GB); Daniel Jon Sall, Greenwood, IN (US); Michael Robert Wiley, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 122 days.

(21) Appl. No.: 10/496,019

(22) PCT Filed: Dec. 9, 2002

(86) PCT No.: PCT/US02/37595

§ 371 (c)(1),
(2), (4) Date: Jun. 1, 2004

(87) PCT Pub. No.: WO03/050109

PCT Pub. Date: Jun. 19, 2003

(65) Prior Publication Data

US 2004/0254374 A1    Dec. 16, 2004

Related U.S. Application Data

(60) Provisional application No. 60/339,325, filed on Dec. 12, 2001.

(51) Int. Cl.
*A61K 31/496* (2006.01)
*C07D 401/04* (2006.01)
*C07D 401/14* (2006.01)

(52) U.S. Cl. .................. 514/253.01; 514/253.09; 514/316; 544/360; 544/364; 546/186; 546/187

(58) Field of Classification Search ............... 544/360, 544/364; 514/253.01, 253.09
See application file for complete search history.

(56) References Cited

FOREIGN PATENT DOCUMENTS

| WO | WO 99/ 11657 | 3/1999 |
|---|---|---|
| WO | WO 99/11658 | 3/1999 |
| WO | WO 00/55154 | 9/2000 |
| WO | WO 00/76971 | 12/2000 |
| WO | WO 01/10425 | 2/2001 |
| WO | WO 01/96323 | 12/2001 |

OTHER PUBLICATIONS

Eberlein et al. Chemical Abstracts, vol. 133, No. 223053, Abstract for WO200055154 (Sep. 21, 2000).*
Jones, Stuart D, et al., Bioorganic & Medicinal Chemistry Letters 11 (2001) 733-736.

* cited by examiner

*Primary Examiner*—Emily Bernhardt
(74) *Attorney, Agent, or Firm*—Thomas E. Jackson

(57) ABSTRACT

Compounds of formula (I)

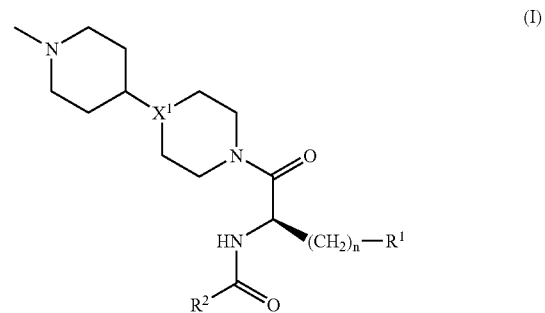

in which $R^1$, $R^2$, n and $X^1$ have the meanings given in the specification are Factor Xa inhibitors useful in the treatment of thrombotic disorders.

14 Claims, No Drawings

ALANYL-PIPERIDINE HETEROCYCLIC DERIVATIVES USEFUL AGAINST CARDIOVASCULAR DISEASES

This application claims the benefit of U.S. provisional patent application Ser. No. 60/339,325 filed on Dec. 12, 2001.

The present invention relates to compounds useful as pharmaceuticals, to pharmaceutical compositions comprising the compounds, to a process for preparing the compounds, to intermediates useful in the preparation of the compounds, and to use of the compounds as pharmaceuticals.

Cardiovascular disease continues to present a major worldwide health problem, and is a common cause of serious illness and death.

One line of investigation being pursued by researchers in the search for new treatments for cardiovascular disease is based upon the hypothesis that an inhibitor of the serine protease, Factor Xa, may be useful as an anticoagulant agent in the treatment of thrombotic disease.

Inhibitors of Factor Xa are known. For example, WO 99/11657, WO 99/11658 and WO 00/76971 disclose certain compounds containing an aromatic group, a glycine residue that bears a cyclic group and a lipophilic group. WO 99/11657, which discloses compounds in which the aromatic group is an aminoisoquinoline group, also generically discloses aminoisoquinoline compounds containing a glycine residue that bears an acyclic group.

Surprisingly, compounds containing particular phenyl, indolyl or benzo[b]thiophenyl groups, a glycine residue bearing a substituted alkyl group and a 4-(1-methylpiperidin-4-yl)piperidin-1-yl or 4-(1-methylpiperidin-4-yl)piperazin-1-yl group have now been found that are selective Factor Xa inhibitors and have particularly advantageous properties.

Accordingly, the present invention provides a compound of formula (I)

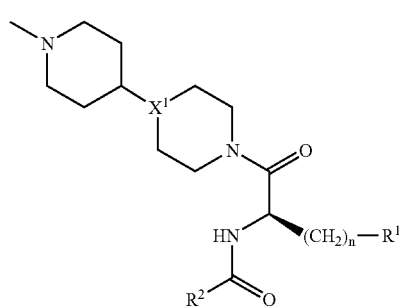

(I)

in which $X^1$ represents CH or N;

n is 1 or 2;

$R^1$ represents trifluoromethyl, COOH, CONH$_2$, SO$_2$NH$_2$, phenyl, pyridyl, C-linked imidazolyl (which may bear an N-(1–4C)alkyl substituent) or a (3–6C)cycloalkyl, oxa(4–6C)cycloalkyl, thia(4–6C)cycloalkyl or C-linked aza(4–6C)cycloalkyl group, which C-linked aza(4–6C)cycloalkyl group may bear an N-(1–4C)alkyl substituent; and $R^2$ is selected from

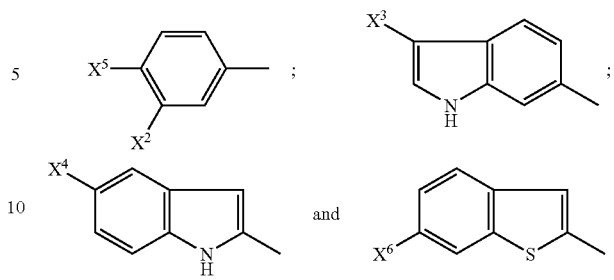

in which $X^2$ represents a hydrogen atom, a halogen atom or an amino group;

$X^3$ represents a hydrogen atom, a methyl group, a fluorine atom, a chlorine atom or a bromine atom;

$X^4$ represents a hydrogen atom, a methyl group or a halogen atom;

$X^5$ represents a chlorine atom, a methoxy group or a methyl group; and $X^6$ represents a hydrogen atom, a halogen atom or a methyl group;

or a pharmaceutically acceptable metabolically labile ester thereof, or a pharmaceutically acceptable salt thereof.

Compounds of formula (I) have been found to be potent and selective inhibitors of the serine protease, Factor Xa, to have good anticoagulant activity in human plasma, to have good plasma exposure upon oral administration to mammals, and to possess particularly advantageous pharmacological and toxicological profiles of activity.

$R^1$ preferably represents trifluoromethyl, COOH, CONH$_2$, phenyl, pyridyl, N-(1–4C)alkylimidazol-4-yl or a cyclopropyl, cyclohexyl, oxetanyl, tetrahydropyranyl, azetidinyl or piperidinyl group, which azetidinyl or piperidinyl group may bear an N-(1–4C)alkyl substituent.

More preferably $R^1$ represents trifluoromethyl, COOH, CONH$_2$, phenyl, pyrid-2-yl, pyrid-3-yl, pyrid-4-yl, N-methylimidazol-4-yl, cyclopropyl, cyclohexyl, tetrahydropyran-4-yl or an N-methylpiperidin-4-yl group.

In the groups represented by $R^2$, $X^2$ preferably represents a hydrogen atom or a halogen atom.

More preferably $X^2$ represents a hydrogen atom or a fluorine atom;

$X^3$ represents a hydrogen atom, a fluorine atom, a chlorine atom or a methyl group;

$X^4$ represents a chlorine atom;

$X^5$ represents a chlorine atom or a methoxy group; and $X^6$ represents a chlorine atom.

Particularly preferred values for $R^2$ are 4-chlorophenyl, 4-methoxyphenyl, 3-fluoro-4-methoxyphenyl, indol-6-yl, 3-methylindol-6-yl, 3-chloroindol-6-yl, 5-fluoroindol-2-yl, 5-chloroindol-2-yl or 6-chlorobenzo[b]thiophen-2-yl.

Especial mention may be made of compounds of formula (I) in which $R^2$ is 4-methoxyphenyl, indol-6-yl or 5-chloroindol-2-yl.

One particular value for $X^1$ is CH. Another is N.

A pharmaceutically acceptable metabolically labile ester of a compound of formula (I) is an ester formed between a carboxyl group (present in compounds of formula (I) when $R^1$ is COOH) and a pharmaceutically acceptable alcohol, which ester is hydrolyzed in vivo to afford the carboxylic acid and the alcohol. Examples of such esters include (1–6C)alkyl esters, such as methyl and ethyl esters.

As used herein, unless otherwise indicated, the term halogen atom includes fluorine, chlorine and bromine.

It will be appreciated that the compounds of formula (I) contain a center of asymmetry that has the (D) configuration. The (D) configuration refers to the configuration of the amino acids from which the compounds may be prepared. The compounds may therefore exist and be isolated in a mixture with the corresponding (L) isomer, such as a racemic mixture, or separately. Preferably the compounds are isolated substantially free of the (L) isomer.

It will also be appreciated that the compounds of formula (I) or their pharmaceutically acceptable salts may be isolated in the form of a solvate, and accordingly that any such solvate is included within the scope of the present invention.

The compounds of formula (I) and their pharmaceutically acceptable salts may be prepared by a process, which comprises (a) reacting a compound of formula (II)

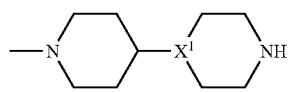
(II)

or a salt thereof, with a compound of formula (III)

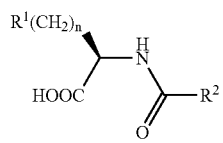
(III)

or a reactive derivative thereof; or (b) reacting a compound of formula (IV)

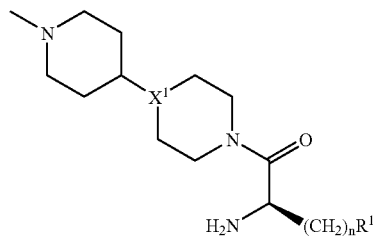
(IV)

or a salt thereof, with a compound of formula (V)

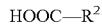 (V)

or a reactive derivative thereof;

followed, if a pharmaceutically acceptable metabolically labile ester or a pharmaceutically acceptable salt is desired, by forming a pharmaceutically acceptable metabolically labile ester or salt.

The reaction between a compound of formula (II) with a compound of formula (III) may conveniently be performed employing reagents and reaction conditions conventionally used for the formation of an amide bond. The reaction is conveniently carried out in the presence of a benzotriazole-based reagent such as 1-hydroxybenzotriazole or 1-hydroxy-7-azabenzotriazole and a dehydrating agent such as dicyclohexylcarbodiimide or 1-(3-dimethylaminopropyl)-3-ethylcarbodiimide, in an inert organic solvent such as dimethylformamide and/or methylene chloride. The reaction is conveniently conducted at a temperature of from 0 to 50° C., preferably at ambient temperature. If a salt of a compound of formula (II) is used, the reaction is conveniently performed in the additional presence of a base such as triethylamine. Other suitable reagents and solvents are known in the art, for example an acid halide, such as the chloride in the presence of a base, such as triethylamine.

The reaction between a compound of formula (IV) with a compound of formula (V) may conveniently be performed employing reagents and reaction conditions conventionally used for the formation of an amide bond. The reaction is conveniently carried out in the presence of a benzotriazole-based reagent such as 1-hydroxybenzotriazole or 1-hydroxy-7-azabenzotriazole and a dehydrating agent such as dicyclohexylcarbodiimide or 1-(3-dimethylaminopropyl)-3-ethylcarbodiimide, in an inert organic solvent such as dimethylformamide and/or methylene chloride. The reaction is conveniently conducted at a temperature of from 0 to 50° C., preferably at ambient temperature. If a salt of a compound of formula (IV) is used, the reaction is conveniently performed in the additional presence of a base such as triethylamine. Other suitable reagents and solvents are known in the art, for example an acid halide, such as p-anisoyl chloride in the presence of a base, such as triethylamine. Alternatively, the compound of formula (IV) may be reacted with a compound of formula (V) in the presence of diethylcyanophosphonate. This reaction is conveniently performed in an organic solvent such as dichloromethane in the presence of a base, such as triethylamine. The temperature is conveniently in the range of from −25 to 25° C.

The compound of formula (II) in which $X^1$ is CH is known, for example from WO 00/76971 at pages 163–164, and is named as 4-(1-methylpiperidin-4-yl)piperidine or 1-methyl-4,4'-bispiperidine.

The compound of formula (II) in which $X^1$ is N is referred to herein as 1-(1-methylpiperidin-4-yl)piperazine.

The compounds of formula (III) may be prepared by reacting a compound of formula (VI)

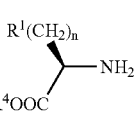
(VI)

in which $R^4$ represents a carboxyl protecting group, for example a (1–6C)alkyl group, such as methyl or ethyl, with a compound of formula (V) to afford a compound of formula (VII)

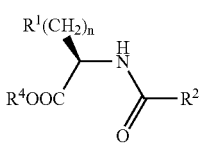
(VII)

followed by removing the protecting group.

The compounds of formula (IV) may be prepared by reacting a compound of formula (II) with a compound of formula (VIII)

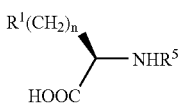

(VIII)

in which $R^5$ represents an amino protecting group, such as t-butoxycarbonyl (Boc) to afford a compound of formula (IX)

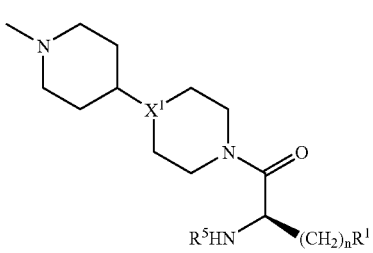

(IX)

followed by removing the protecting group.

The compounds of formulae (VI) and (VIII) are known or may be prepared using conventional methods for the preparation of amino acids protected on the carboxy or amino group. Particular preparations are also described in the Examples.

The compounds of formula (V) are well known.

The protection of amino and carboxylic acid groups is described in McOmie, Protecting Groups in Organic Chemistry, Plenum Press, NY, 1973, and Greene and Wuts, Protecting Groups in Organic Synthesis, 2nd. Ed., John Wiley & Sons, NY, 1991. Examples of carboxy protecting groups include $C_1$–$C_6$ alkyl groups such as methyl, ethyl, t-butyl and t-amyl; aryl($C_1$–$C_4$)alkyl groups such as benzyl, 4-nitrobenzyl, 4-methoxybenzyl, 3,4-dimethoxybenzyl, 2,4-dimethoxybenzyl, 2,4,6-trimethoxybenzyl, 2,4,6-trimethylbenzyl, benzhydryl and trityl; silyl groups such as trimethylsilyl and t-butyldimethylsilyl; and allyl groups such as allyl and 1-(trimethylsilylmethyl)prop-1-en-3-yl.

Examples of amine protecting groups include acyl groups, such as groups of formula RCO in which R represents $C_{1-6}$ alkoxy, phenyl $C_{1-6}$ alkoxy, or a $C_{3-10}$ cycloalkoxy, wherein a phenyl group may be optionally substituted, for example by one or two of halogen, $C_1$–$C_4$ alkyl and $C_1$–$C_4$ alkoxy.

Preferred amino protecting groups include benzyloxycarbonyl (CBz) and t-butoxycarbonyl (Boc).

Certain of the intermediates described herein, for example the compounds of formulae (III) and (IV), are believed to be novel and accordingly are provided as further aspects of the invention.

The compounds of the invention may be administered by any convenient route, e.g. into the gastrointestinal tract (e.g. rectally or orally), the nose, lungs, musculature or vasculature or transdermally. The compounds may be administered in any convenient administrative form, e.g. tablets, powders, capsules, solutions, dispersions, suspensions, syrups, sprays, suppositories, gels, emulsions, patches etc. Such compositions may contain components conventional in pharmaceutical preparations, e.g. diluents, carriers, pH modifiers, sweeteners, bulking agents, and further active agents. If parenteral administration is desired, the compositions will be sterile and in a solution or suspension form suitable for injection or infusion. Such compositions form a further aspect of the invention.

Viewed from this aspect the invention provides a pharmaceutical composition, which comprises the compound of formula (I) or a pharmaceutically acceptable salt thereof, together with a pharmaceutically acceptable diluent or carrier.

According to another aspect, the present invention provides the compound of formula (I) or a pharmaceutically acceptable salt thereof, for use in therapy.

According to another aspect, the present invention provides the use of the compound of formula (I) or a pharmaceutically acceptable salt thereof, for the manufacture of a medicament for the treatment of a thrombotic disorder.

According to another aspect, the present invention provides a method of treating a thrombotic disorder in a subject requiring treatment, which comprises administering an effective amount of a compound of formula (I) or a pharmaceutically acceptable salt thereof.

The subject may be a human or a non-human animal, such as a non-human mammal, for example a cat, dog, horse, cow or sheep.

The thrombotic disorder may be, for example, venous thrombosis, pulmonary embolism, arterial thrombosis, myocardial ischaemia, myocardial infarction or cerebral thrombosis. A particular indication is, for example, prophylaxis of post-operative venous thrombosis following high risk orthopedic surgery (such as hip or knee replacement), primary treatment of venous thrombosis, secondary prevention of ischemic cardiovascular complications following myocardial infarction (in combination with e.g. low dose aspirin), or prevention of embolic stroke in non-valvular atrial fibrillation. The compounds may also be used in accordance with the method of the invention in the treatment of acute vessel closure associated with thrombolytic therapy and restenosis, for example after transluminal coronary angioplasty or bypass grafting of the coronary or peripheral arteries, and in the maintenance of vascular access patency in long term hemodialysis patients.

The dosage of the compound of formula (I) will depend upon the nature and severity of the condition being treated, the administration route and the size and species of the subject. In general, quantities in the range of from 0.01 to 100 μM/kg bodyweight will be administered.

As used herein, the term "treatment" includes prophylactic use. The term "effective amount" refers to the amount of the compound of formula (I) that is effective to reduce or inhibit the development of the symptoms of the thrombotic disorder being treated.

The compound according to the invention may be administered alone or in combination with an anticoagulant having a different mode of action or with a thrombolytic agent.

The following Examples illustrate the invention.

API-MS (atmospheric pressure chemical ionization mass spectra) were obtained on a PESciex API 150EX with a heated nebulizer and nitrogen as the reagent gas in positive ion mode.

CI-MS (Chemical ionization mass spectra) were obtained on a Shimadzu 5000 direct insertion mass spectrometer in chemical ionization mode utilizing methane as the reagent gas.

TLC performed on AnalTech No. 02521 silica gel plates.

The following abbreviations are used throughout: Abbreviations used follow IUPAC-IUB nomenclature. Additional abbreviations are Boc, tertiary-butyloxycarbonyl; CMA, chloroform: methanol: concentrated ammonium hydroxide (80:18:2); DEPC, diethyl cyanophosphonate. DCC, dicyclohexylcarbodiimide; DIEA, N,N-diisopropylethylamine; DMSO, dimethyl sulfoxide (perdeuterated if for NMR); DMF, dimethylformamide; EDCI, 1-[3-(dimethylamino) propyl]-3-ethylcarbodiimide hydrochloride; ES-MS, electrospray mass spectrum; LCMS, liquid chromatography mass spectrum; EtOAc, ethyl acetate; Et$_2$O, diethyl ether; HOAt, 1-hydroxy-7-aza-benzotriazole; HOBt, 1-hydroxybenzotriazole; HPLC, high pressure liquid chromatography; MeOH, methanol; SCX, strong cation exchange; TEA, triethylamine; TFA, trifluoroacetic acid; and THF, tetrahydrofuran. Reagents were obtained from a variety of commercial sources.

Method 1: A solution or suspension of an amine or amine hydrochloride salt (1 eq, approximately 0.2 M) in THF, dichloromethane, or DMF (or a mixture of any of these solvents) is treated with a carboxylic acid (approximately 1 eq), either HOBt or HOAt (approximately 1 eq), either TEA or DIEA (0–3 eq), and either EDCI or DCC (approximately 1 eq). After stirring overnight at room temperature, the solvents are removed and the residue is diluted with ethyl acetate or dichloromethane and washed with saturated aqueous sodium bicarbonate and brine. The organic solution is then dried with MgSO$_4$, filtered and concentrated in vacuo. If necessary, the product is purified by chromatography over silica gel, eluting with a gradient of 0% through 2 to 12% 2 N ammonia/methanol in dichloromethane or chloroform. The product-containing fractions are then combined and concentrated in vacuo.

Method 2: To a stirring solution of an amine or amine hydrochloride salt (1 eq), triethylamine (1–3 eq), and a carboxylic acid (about 1.2 eq) in dichloromethane (0.2–0.5 M) at 0° C., is slowly added diethyl cyanophosphonate (about 1.2 eq). After stirring overnight, the solvents are removed in vacuo; and the residue is partitioned between water and an organic solvent such as ethyl acetate or dichloromethane and washed with saturated aqueous NaHCO$_3$, followed by brine. The organic phase is then dried with MgSO$_4$ or Na$_2$SO$_4$, filtered and concentrated in vacuo. If necessary, the product is purified by chromatography over silica gel, eluting with a gradient of 0–10% 2 N ammonia/methanol in either dichloromethane or chloroform. The product-containing fractions are then combined and concentrated in vacuo.

Method 3: The amine or amine hydrochloride salt (1 eq) and triethylamine (1–3 eq) are dissolved in dichloromethane (0.2–0.5 M) and an acid chloride (about 1.2 eq) is added. After stirring for about 3 h, the volatiles are removed in vacuo; and the residue is dissolved in methanol (possibly with an organic cosolvent such as dichloromethane) and loaded onto a strong cation exchange (SCX) column. The column is washed with methanol, and then the desired product is eluted from the column with a solution of ammonia or triethylamine in methanol (possibly with an organic cosolvent such as dichloromethane). The product containing fractions are then combined and concentrated in vacuo. If necessary, the product is purified further by chromatography over silica gel, eluting with a gradient of 0–10% 2 N ammonia/methanol in either dichloromethane or chloroform. The product-containing fractions are then combined and concentrated in vacuo.

Method 5: A solution or suspension of an amine or amine hydrochloride salt (1 eq, approximately 0.2 M) in THF, dichloromethane, or DMF (or a mixture of any of these solvents) is treated with a carboxylic acid (approximately 1 eq), and either TEA or DIEA (0–3 eq) and mixed several minutes. Either HOBt or HOAt (approximately 1 eq) and either EDCI or DCC (approximately 1 eq) are separately stirred together in a solvent; and the resulting mixture is added to the other solution, or vice versa. After stirring overnight at room temperature, either the solvents are removed and the residue is diluted with ethyl acetate or dichloromethane, or the reaction solution is partitioned between the reaction solvent and saturated aqueous sodium bicarbonate, separated, and the organics washed with saturated aqueous sodium bicarbonate and saturated brine. The organic solution is then dried with MgSO$_4$, filtered and concentrated in vacuo. If necessary, the product is purified by chromatography over silica gel, eluting with a gradient of 0% through 2 to 12% 2 N ammonia/methanol in dichloromethane or chloroform. The product-containing fractions are then combined and concentrated in vacuo.

General Deprotection Methods

Method 1: A solution of the t-butylcarbamate (1 eq) in CH$_2$Cl$_2$ (0.2 M) is treated with anisole (5 eq) and TFA (20% by volume). After stirring 1 to 3 h at ambient temperature, the reaction mixture is concentrated in vacuo. The crude residue is purified by strong cation exchange chromatography (SCX). The SCX column is washed with a 5% solution of acetic acid in methanol and the TFA salt is dissolved in methanol (possibly with a cosolvent such as dichloromethane) and loaded onto the SCX column. The column is then washed with methanol (possibly with a cosolvent such as dichloromethane), and then the free base is eluted from the column with a 2 N solution of ammonia or triethylamine in methanol (possibly with a cosolvent such as dichloromethane). The product containing fractions are then combined and concentrated in vacuo to give the product in the free base form.

Method 2: HCl gas is bubbled into a solution of the t-butylcarbamate in anhydrous MeOH (0.1 M) for approximately 10 to 30 min, then the reaction mixture is either concentrated in vacuo or filtered immediately and washed with ether to give the HCl salt of the title amine.

General HCl Salt Formation Methods

Method 1: The free base is dissolved in 0.2 N aqueous HCl (1–2 eq of HCl). The resulting solution is freeze-dried to give the amine hydrochloride salt.

Method 2: A solution of the free base in a small amount of CH$_2$Cl$_2$ is treated with 1.0–2.2 equivalents of 1 M HCl in ether. After stirring 30 min, the reaction mixture is filtered, and the resulting solid is rinsed with ether and dried to give the amine hydrochloride salt.

General Analytical HPLC Methods

Method 1: Vydac C18 (4.6×250 mm) or Symmetry (4.6×150 mm), elute with a linear gradient of 90/10 through 50/50 (0.1% TFA in water/0.1% TFA in acetonitrile) over 45 min, 1 mL/min, λ=214 nm.

Method 2: Vydac C18 (4.6×250 mm), elute with a linear gradient of 90/10 through 50/50 (0.1% TFA in water/0.1% TFA in acetonitrile) over 20 or 40 min, 1 mL/min, λ=all.

HPLC Analysis (Method A): Waters Symmetry, C18 (4.6×250 mm) column. The elution system consisted of linear gradient from 95:5 (0.1% TFA in H$_2$O)/(0.1% TFA in CH$_3$CN) to 5:95 (0.1% TFA in H$_2$O)/(0.1% TFA in CH$_3$CN) over 20 min, followed by 5:95 (0.1% TFA in H$_2$O)/(0.2% TFA in CH$_3$CN) isocratic over 15 min. The flow rate was 1 mL/min. UV Detection was performed at 254 nm unless otherwise noted.

PREPARATION OF COMPOUNDS OF FORMULA (VIII)

Preparation (VIII)-1

N-Boc-β-(1-Methylpiperidin-4-yl)-D-alanine

A. N-Boc-D-β-(1-methylpyridin-4-ium)alanine iodide

A mixture of N-Boc-β-(4-pyridyl)-D-alanine (4.0 g, 15.02 mmol) and iodomethane (3.19 g, 22.53 mmol) in acetone (50 mL) was heated at reflux for 16 h. The suspension was then concentrated under reduced pressure to give N-Boc-β-(1-methylpyridin-4-ium)-D-alanine iodide as a yellow foam (6.13 g, quantitative).

$^1$H NMR (CD$_3$OD).
APCI-MS, m/e=283 [C$_{14}$H$_{21}$N$_2$O$_4$+1].

B. N-Boc-β-(1-Methylpiperidin-4-yl)-D-alanine

A mixture of N-Boc-β-(1-methylpyridin-4-ium)-D-alanine iodide (6.1 g, 14.94 mmol) and platinum(IV) oxide (0.10 g, 0.44 mmol) in methanol (50 mL) was placed under a hydrogen atmosphere (2.04 bar, 30 psi) for 16 h on a Parr hydrogenation apparatus. The mixture was filtered over diatomaceous earth and poured over 50 g of SCX resin (activated with 5% acetic acid/methanol). The resin was washed with methanol (100 mL) and flushed with saturated ammonia in methanol solution (100 mL). The basic fraction was concentrated under reduced pressure to give the subtitled compound as a white foam (4.19 g, 98%).

$^1$H NMR (CD$_3$OD).
APCI-MS, m/e=287 [C$_{14}$H$_{26}$N$_2$O$_4$+1].

PREPARATION OF COMPOUNDS OF FORMULA (IX)

Preparation (IX)-1

1-(N-Boc-β-Phenyl-D-alanyl)-4-(1-methylpiperidin-4-yl)piperazine

Prepared from Boc-β-phenyl-D-alanine and 1-(1-methylpiperidin-4-yl)piperazine using methods substantially equivalent to General Coupling Method 5.

$^1$H NMR.
ES-MS, m/z 430.3 (M+1)$^+$.
Analysis for C$_{25}$H$_{39}$N$_3$O$_3$.1.3H$_2$O. Calcd: C, 66.28; H, 9.26; N, 9.27. Found: C, 66.07; H, 8.79; N, 9.28.

Preparation (IX)-2

1- [N-Boc-(γ-Benzyl)-D-glutamyl]-4-(1-methylpiperidin-4-yl)piperidine

Prepared from N-Boc-D-glutamatic acid γ-benzyl ester and 4-(1-methylpiperidin-4-yl)piperidine dihydrobromide using methods substantially equivalent to General Coupling Method 1.

$^1$H NMR.
ES-MS, m/z 502.4(M+1)$^+$.
Analysis For C$_{28}$H$_{43}$N$_3$O$_5$.1.0H$_2$O: Calcd: C, 64.71; H, 8.73; N, 8.09. Found: C, 65.07; H, 8.43; N, 8.47.

Preparation (IX)-3

1-[N-Boc-(β-Benzyl)-D-aspartyl]-4-(1-methylpiperidin-4-yl)piperidine

Prepared from N-Boc-D-aspartic acid β-benzyl ester and 4-(1-methylpiperidin-4-yl)piperidine dihydrobromide using methods substantially equivalent to General Coupling Method 1.

$^1$H NMR.
ES-MS, m/z 488.4(M+1)$^+$.
Analysis For C$_{21}$H$_{39}$N$_3$O$_4$.1.0H$_2$O: Calcd: C, 66.50; H, 8.47; N, 8.62. Found: C, 65.85; H, 8.19; N, 8.71.

Preparation (IX)-4

1-[N-Boc-β-(3-Pyridinyl)-D-alanyl]-4-(1-methylpiperidin-4-yl)piperidine

Method B-1: To a suspension of N-Boc-β-(3-pyridinyl)-D-alanine (1.0 g, 3.76 mmol) and 4-(1-methylpiperidin-4-yl)piperidine dihydrobromide (1.18 g, 3.42 mmol) in anhydrous dichloromethane (30 mL) under nitrogen atmosphere was added DEPC (0.66 g, 4.10 mmol) at −15° C. The mixture was stirred for 20 min; then N,N-diisopropylethylamine was added. The mixture was stirred for 16 h at room temperature. The organic layer was washed with 20 mL portions of saturated aqueous sodium bicarbonate solution, water and brine. The organic layer was subsequently dried over sodium sulfate, filtered, and concentrated under reduced pressure to give a crude yellow oil. The oil was purified by flash column chromatography over silica gel, eluting with dichloromethane/CMA (10:1 to 3:1), to give the titled compound as a colorless gum (0.56 g, 38%).

$^1$H NMR (CDCl$_3$).
APCI-MS, m/e=431 (M+1).

Preparation (IX)-5

1-[N-Boc-β-(4-Pyridinyl)-D-alanyl]-4-(1-methylpiperidin-4-yl)piperidine

Using methods substantially equivalent to those described in Method B-1, the titled compound was prepared from N-Boc-β-(4-pyridinyl)-D-alanine and 4-(1-methylpiperidin-4-yl)piperidine dihydrobromide (44%).

$^1$H NMR (CDCl$_3$).
APCI-MS, m/e=431 (M+1).

Preparation (IX)-6

1-[N-Boc-β-(2-Pyridinyl)-D-alanyl]-4-(1-methylpiperidin-4-yl)piperidine

Using methods substantially equivalent to those described in Method B-1, the titled compound was prepared from N-Boc-β-(2-pyridinyl)-D-alanine and 4-(1-methylpiperidin-4-yl)piperidine dihydrobromide (33%).

$^1$H NMR (CDCl$_3$).
APCI-MS, m/e=431 (M+1).

Preparation (IX)-7

1-(N-Boc-1-Methyl-D-histidinyl)-4-(1-methylpiperidin-4-yl)piperidine

Using methods substantially equivalent to those described in Method B-2, the subtitled compound was prepared from N-Boc-1-methyl-D-histidine and 4-(1-methylpiperidin-4-yl)piperidine (72%).
$^1$H NMR (CDCl$_3$).
APCI-MS, m/e 434 (C$_{23}$H$_{39}$N$_5$O$_3$+1).

Preparation (IX)-8

1-[N-Boc-β-Cyclohexyl-D-alanyl]-4-(1-methylpiperidin-4-yl)piperidine

Method B-3: To a mixture of N-Boc-β-cyclohexyl-D-alanine (1.0 g, 3.7 mmol), 4-(1-methylpiperidin-4-yl)piperidine dihydrobromide (1.5 g, 4.47 mmol), HOBt (0.5 g, 3.7 mmol) and EDCI (0.85 g, 4.43 mmol) in DMF (5.6 mL) was added diisopropylethylamine (2.6 mL, 16 mmol); and the mixture stirred overnight at room temperature. The solvent was removed under vacuum. The residue was suspended in water and extracted with dichloromethane. The organic layer was washed with water, dried over anhydrous sodium sulfate, filtered, and concentrated under vacuum. The residue was purified by chromatography on silica gel with dichloromethane/CMA to provide the titled compound (600 mg, 34%).
$^1$H NMR (CDCl$_3$).
APCI-MS, m/e=436 (M+1).

Preparation (IX)-9

1-[N-Boc-β-(4-tetrahydropyranyl)alanyl]-4-(1-methylpiperidin-4-yl)piperidine Using methods substantially equivalent to that described in Method B-3, the titled compound was prepared from N-Boc-β-(4-tetrahydropyranyl)alanine and 4-(1-methylpiperidin-4-yl)piperidine (22%).
$^1$H NMR (CDCl$_3$).
APCI-MS, m/e=438 (M+1).

Preparation (IX)-10

1-(N-Boc-β-Cyclohexyl-D-alanyl)-4-(1-methylpiperidin-4-yl)piperazine

Prepared from Boc-β-cyclohexyl-D-alanine and 1-(1-methylpiperidin-4-yl)piperazine using methods substantially equivalent to General Coupling Method 1.
$^1$H NMR.
ES-MS, m/z 437.5 (M+1)$^+$.
Analysis For C$_{24}$H$_{44}$N$_4$O$_3$·1.0H$_2$O. Calcd: C, 63.40; H, 10.20; N, 12.32. Found: C, 63.84; H, 9.78; N, 12.69.

Preparation (IX)-11

1-[N-Boc-β-(4-Tetrahydropyranyl)alanyl]-4-(1-methylpiperidin-4-yl)piperazine Prepared from N-Boc-β-(4-tetrahydropyranyl)alanine and 1-(1-methylpiperidin-4-yl)piperazine using methods substantially equivalent to General Coupling Method 1.
$^1$H NMR.
ES-MS, 439.4 m/z (M+1)$^+$.
Analysis for C$_{23}$H$_{42}$N$_4$O$_4$·1.0H$_2$O. Calcd: C, 60.50; H, 9.71; N, 12.27. Found: C, 61.08; H, 9.26; N, 12.86.

Preparation (IX)-12

1-[N-Boc-β-(4-Pyridinyl)-D-alanyl]-4-(1-methylpiperidin-4-yl)piperazine

Method B-2: To a solution of N-Boc-β-(4-pyridyl)-D-alanine (3.0 g, 11.3 mmol) and 1-(1-methylpiperidin-4-yl)piperazine (2.07 g, 11.3 mmol) in anhydrous N,N-dimethylformamide (20 mL) under nitrogen atmosphere at 0° C. was added HOBt (1.52 g, 11.3 mmol) followed by N,N-diisopropylethylamine (2.91 g, 22.5 mmol). 1-[3-(Dimethylamino)propyl]-3-ethylcarbodiimide hydrochloride (2.37 g, 12.4 mmol) was added, and the mixture stirred for 16 h at room temperature. The mixture was diluted with water (100 mL) and washed four times with 50 mL portions of chloroform/2-propanol (3:1). The organic layer was washed with 50-mL portions of water and brine and dried over anhydrous sodium sulfate. The organic layer was filtered and concentrated under reduced pressure to give a crude oil. The oil was purified by flash chromatography, eluting with dichloromethane/CMA (50:1 to 3:1), to give the titled compound as a white foam (3.88 g, 80%).
$^1$H NMR (CDCl$_3$).
APCI-MS, m/e=432 (M+1).

Preparation (IX)-13

1-[N-Boc-β-(2-Pyridinyl)-D-alanyl]-4-(1-methylpiperidin-4-yl)piperazine

Using methods substantially equivalent to those described in Method B-2, the titled compound was prepared from N-Boc-β-(2-pyridinyl)-D-alanine and 1-(1-methylpiperidin-4-yl)piperazine (72%).
$^1$H NMR (CDCl$_3$).
APCI-MS, m/e=432 (M+1).

Preparation (IX)-14

1-(N-Boc-D-Glutamyl)-4-(1-methylpiperidin-4-yl)piperazine

Using methods substantially equivalent to those described in Method B-2, the titled compound was prepared from N-Boc-D-glutamine and 1-(1-methylpiperidin-4-yl)piperazine (67%).
$^1$H NMR (CDCl$_3$).
APCI-MS, m/e=412 (M+1).

Preparation (IX)-15

1-[N-Boc-β-(1-Methylpiperidin-4-yl)-D-alanyl]-4-(1-methylpiperidin-4-yl)piperazine Using methods substantially equivalent to those described in Method B-2, the titled compound was prepared from N-Boc-β-(1-methylpiperidin-4-yl)-D-alanine and 1-(1-methylpiperidin-4-yl)piperazine (57%).
$^1$H NMR (CDCl$_3$).
APCI-MS, m/e=452 (M+1).

Preparation (IX)-16

1-(N-Boc-D-Asparaginyl)-4-(1-methylpiperidin-4-yl)piperazine

Using methods substantially equivalent to those described in Method B-2, the titled compound was prepared from N-Boc-D-asparagine and 1-(1-methylpiperidin-4-yl)piperazine (66%).

$^1$H NMR (CDCl$_3$).
APCI-MS, m/e=398 (M+1).

Preparation (IX)-17

1-[N-Boc-β-(Trifluoromethyl)-D/L-alanyl-4-(1-methylpiperidin-4-yl)piperazine

Boc-D,L-trifluoromethylalanine (1.3 g, 5.05 mmole), (1-methylpiperidin-4-yl)piperazine (0.77 g, 4.21 mmole), HOAt (0.74 g, 5.47 mmole), EDCI (1.05 g, 5.47 mmole) and triethylamine (1.4 ml, 10 mmole) were dissolved in DMF (30 ml) and stirred overnight at room temperature. All volatiles were removed under high vacuum and the residue partitioned between sat. aqueous sodium bicarbonate and 4:1 chloroform/isopropyl alcohol. The organic solution was washed with brine, dried (MgSO$_4$) and concentrated in vacuo. The oil obtained was purified by flash chromatography (SiO2, DCM:MeOH:10%:ammonia solution—80:10:10) to give 1-(Boc-D,L-trifluoromethylalaninyl)-4-(1-methylpiperidin-4-yl)piperazine (0.83 g).

$^1$H NMR
LCMS 423 (M+1)$^+$

Preparation (IV)-1

1-(β-Phenyl-D-alanyl)-4-(1-methylpiperidin-4-yl)piperidine

Prepared from 1-(N-Boc-β-phenyl-D-alanyl)-4-(1-methylpiperidin-4-yl)piperidine using methods substantially equivalent to General Deprotection Method 1.

$^1$H NMR (DMSO-$_{d6}$) 10.8 (bs, 1 H), 8.42 (m, 3 H), 7.29 (m, 5 H), 4.60 (bs, 1 H), 4.38 (bd, J=12.8 Hz, 1 H), 4.09 (bs, 1 H), 3.63 (m, 1 H), 3.33 (d, J=11.7 Hz, 2 H), 3.2 (m 1 H), 2.96–2.74 (m, 3 H), 2.64 (d, J=4.4 Hz, 3 H), 2.37 (m, 1 H), 2.20 (m, 0.5 H), 1.8–0.8 (m, 8.5 H), 0.63 (m, 0.5 H), −0.29 (m, 0.5 H).
MS (ES+) 329.2 m/z

Preparation (IV)-2

1-[(γ-Methyl)-D-glutamyl]-4-(1-methylpiperidin-4-yl)piperidine Dihydrochloride

Prepared from 1-[N-Boc-(γ-benzyl)-D-glutamyl]-4-(1-methylpiperidin-4-yl)piperidine using methods substantially equivalent to those described in General Deprotection Method 2, which resulted in removal of the Boc group and transesterification of the ester.

$^1$H NMR.
ES-MS, m/z 326.5 (M+1)$^+$.

Preparation (IV)-3

1-[(β-Benzyl)-D-aspartyl]-4-(1-methylpiperidin-4-yl)piperidine Hydrochloride

Prepared from 1-[N-Boc-(β-benzyl)-D-aspartyl]-4-(1-methylpiperidin-4-yl)piperidine using methods substantially equivalent to those described in General Deprotection Method 2.

$^1$H NMR.
ES-MS, m/z 388.5 (M+1)$^+$.
Analysis For C$_{22}$H$_{33}$N$_3$O$_3$.2.0HCl.1.7H$_2$O. Calcd: C, 53.81; H, 7.88; N, 8.56 Cl, 14.40. Found: C, 53.40; H, 8.15; N, 8.61 Cl, 14.16.

Preparation (IV)-4

1-[β-(3-Pyridinyl)-D-alanyl]-4-(1-methylpiperidin-4-yl)piperidine Trihydrochloride

Method C-1: To a solution of 1-[N-Boc-β-(3-pyridinyl)-D-alanyl)-4-(1-methylpiperidin-4-yl)piperidine (0.740 g, 1.71 mmol) and anisole (4.08 g, 37.8 mmol) in methanol (10 mL) was added concentrated hydrochloric acid (2.0 mL) at 0° C. The mixture was stirred for 5 h at room temperature. The mixture was concentrated under reduced pressure to give the titled compound as a white foam (0.739 g, quantitative).

$^1$H NMR (CD$_3$OD).
APCI-MS, m/e=331 (C$_{19}$H$_{30}$N$_4$O+1).

Preparation (IV)-5

1-[β-(4-Pyridinyl)-D-alanyl]-4-(1-methylpiperidin-4-yl)piperidine Trihydrochloride

Using methods substantially equivalent to those described in Method C-1, the titled compound was prepared from 1-[N-Boc-β-(4-pyridinyl)-D-alanyl]-4-(1-methylpiperidin-4-yl)piperidine (quantitative).

$^1$H NMR (CD$_3$OD).
APCI-MS, m/e=331 (C$_{19}$H$_{30}$N$_4$O+1).

Preparation (IV)-6

1-[β-(2-Pyridinyl)-D-alanyl]-4-(1-methylpiperidin-4-yl)piperidine Trihydrochloride

Using methods substantially equivalent to those described in Method C-1, the subtitled compound was prepared from 1-[N-Boc-β-(2-pyridinyl)alanyl]-4-(1-methylpiperidin-4-yl)piperidine (quantitative).

$^1$H NMR (CD$_3$OD).
APCI-MS, m/e=331 (C$_{19}$H$_{30}$N$_4$O+1).

Preparation (IV)-7

1-(1-Methyl-D-histidinyl)-4-(1-methylpiperidin-4-yl)piperidine Trihydrochloride

Using methods substantially equivalent to those described in Method C-1, the subtitled compound was prepared from 1-(N-Boc-1-methyl-D-histidinyl)-4-(1-methylpiperidin-4-yl)piperidine (72%).

$^1$H NMR (CD$_3$OD).
APCI-MS, m/e 334 (C$_{18}$H$_{31}$N$_5$O+1).

Preparation (IV)-8

1-(β-Cyclohexyl-D-alanyl)-4-(1-methylpiperidin-4-yl)piperidine Dihydrochloride Method C-2: A mixture of 1-(N-Boc-β-cyclohexyl-D-alanyl)-4-(1-methylpiperidin-4-yl)piperidine (3.4 g, 9 mmol), methanol (50 mL), and anisole (15 mL) was cooled to 0° C. Concentrated HCl (20 mL) was added. The mixture was stirred 2 h at room temperature. The mixture was concentrated under vacuum and the residue triturated in diethyl ether. The solids were collected by vacuum filtration to provide the subtitled compound as a white solid (0.55 g, 98%).
$^1$H NMR (CD$_3$OD).
APCI-MS, m/e=336 (M+1).

Preparation (IV)-9

1-[β-(4-Tetrahydropyranyl)alanyl]-4-(1-methylpiperidin-4-yl)piperidine Dihydrochloride Using methods substantially equivalent to that described in Method C-2, the titled compound was prepared from 1-(N-Boc-β-(4-tetrahydropyranyl)alanyl]-4-(1-methylpiperidin-4-yl)piperidine (98%).
$^1$H NMR (CD$_3$OD).
APCI-MS, m/e=338 (M+1).

Preparation (IV)-10

1-(β-Cyclohexyl-D-alanyl)-4-(1-methylpiperidin-4-yl)piperazine Hydrochloride Prepared from 1-(N-Boc-β-cyclohexyl-D-alanyl)-4-(1-methylpiperidin-4-yl)piperazine using methods substantially equivalent to those described in General Deprotection Method 2.
$^1$H NMR.
ES-MS, m/z 337.3 (M+1)$^+$.
Analysis For C$_{19}$H$_{36}$N$_4$O.3.0HCl.2.0H$_2$O: Calcd: C, 47.35; H, 8.99; N, 11.63. Found: C, 47.73; H, 8.28; N, 11.79.

Preparation (IV)-11

1-[β-(4-Tetrahydropyranyl)alanyl]-4-(1-methylpiperidin-4-yl)piperazine Hydrochloride Prepared from 1-[N-Boc-β-(4-tetrahydropyranyl)alanyl]-4-(1-methylpiperidin-4-yl)piperazine using methods substantially equivalent to those described in General Deprotection Method 2.
$^1$H NMR.
ES-MS, m/z 339.4 (M+1)$^+$.
Analysis For C$_{18}$H$_{34}$N$_4$O$_2$.3.0HCl.4.0H$_2$O: Calcd: C, 41.58; H, 8.72; N, 10.78 Cl, 20.46. Found: C, 41.40; H, 7.58; N, 10.81 Cl, 20.54.

Preparation (IV)-12

1-[β-(4-Pyridinyl)-D-alanyl]-4-(1-methylpiperidin-4-yl)piperazine Tetrahydrochloride Using methods substantially equivalent to those described in Method C-1, the titled compound was prepared from 1-[N-Boc-β-(4-pyridinyl)-D-alanyl]-4-(1-methylpiperidin-4-yl)piperazine (quantitative).
$^1$H NMR (CD$_3$OD).
APCI-MS, m/e=333 (C$_{18}$H$_{29}$N$_5$O+1).

Preparation (IV)-13

1-[β-(2-Pyridinyl)-D-alanyl]-4-(1-methylpiperidin-4-yl)piperazine Tetrahydrochloride Using methods substantially equivalent to those described in Method C-1, the titled compound was prepared from 1-[N-Boc-β-(2-pyridinyl)-D-alanyl]-4-(1-methylpiperidin-4-yl)piperazine (quantitative).
$^1$H NMR (CD$_3$OD).
APCI-MS, m/e=333 (C$_{18}$H$_{29}$N$_5$O+1).

Preparation (IV)-14

1-(D-Glutamyl)-4-(1-methylpiperidin-4-yl)piperazine Trihydrochloride

Using methods substantially equivalent to those described in Method C-2, the subtitled compound was prepared from 1-(N-Boc-D-glutamyl)-4-(1-methylpiperidin-4-yl)piperazine (quantitative).
$^1$H NMR (CD$_3$OD).
APCI-MS, m/e=315 (C$_{15}$H$_{29}$N$_5$O$_2$+1).

Preparation (IV)-15

1-[β-(1-Methylpiperidin-4-yl)-D-alanyl]-4-(1-methylpiperidin-4-yl)piperazine Tetrahydrochloride Using methods substantially equivalent to those described in Method C-2, the titled compound was prepared from 1-[N-Boc-β-(1-methylpiperidin-4-yl)-D-alanyl]-4-(1-methylpiperidin-4-yl)piperazine (quantitative).
$^1$H NMR (CD$_3$OD).
APCI-MS, m/e=354 (C$_{19}$H$_{37}$N$_5$O+1).

Preparation (IV)-16

1-(D-Asparaginyl)-4-(1-methylpiperidin-4-yl)piperazine Trihydrochloride

Using methods substantially equivalent to those described in Method C-2, the titled compound was prepared from 1-(N-Boc-D-asparaginyl)-4-(1-methylpiperidin-4-yl)piperazine (quantitative).
$^1$H NMR (CD$_3$OD).
APCI-MS, m/e=353 (C$_{14}$H$_{27}$N$_5$O$_2$+1).

Preparation (IV)-17

1-β-(Trifluoromethyl)-D/L-alanyl-4-(1-methylpiperidin-4-yl)piperazine 1-(Boc-D,L-trifluoromethylalaninyl)-4-(1-methylpiperidin-4-yl)piperazine (0.83 g) was dissolved in ethyl acetate (30 ml) and HCl gas bubbled in for 10 min. Methanol (20 ml) was added to help dissolve the precipitate formed. When the reaction was complete (LCMS) the solution was evaporated to dryness to give the trihydrochloride salt (840 mg). This was converted to the free base by absorption onto an SCX ion exchange column and elution with a solution of ammonia in methanol/dichloromethane to give 1-(D,L-trifluoromethylalaninyl)-4-(1-methylpiperidin-4-yl)piperazine 660 mg.
$^1$H NMR.

EXAMPLE 1

1-[N-(Indole-6-carbonyl)-β-phenyl-D-alanyl]-4-(1-methylpiperidin-4-yl)piperidine Hydrochloride Prepared from 1-(β-phenyl-D-alanyl)-4-(1-methylpiperidin-4-yl)piperidine hydrochloride and indole-6-carboxylic acid using methods substantially equivalent to General Coupling Method 5. The HCl salt is prepared following Salt Formation Method 2.

$^1$H NMR.

ES-MS, m/z 476.3 (M+1)$^+$; 471.1 (M−1)$^−$.

Analysis For $C_{29}H_{36}N_4O_2 \cdot 1.0HCl \cdot 2.0H_2O$. Calcd: C, 63.90; H, 7.58; N, 10.28; Cl, 6.50. Found: C, 63.93; H, 7.26; N, 10.00; Cl, 6.35.

Analytical HPLC (Method 1): >96%, $t_r$=25.4 min.

EXAMPLE 2

1-[N-(4-Methoxybenzoyl)-β-phenyl-D-alanyl]-4-(1-methylpiperidin-4-yl)piperidine Hydrochloride Prepared from 1-(β-phenyl-D-alanyl)-4-(1-methylpiperidin-4-yl)piperidine hydrochloride and 4-methoxybenzoic acid using methods substantially equivalent to General Coupling Method 5. The HCl salt is prepared following Salt Formation Method 2.

$^1$H NMR.

ES-MS, m/z 464.1 (M+1)$^+$.

Analysis For $C_{28}H_{37}N_3O_3 \cdot 1.5HCl$. Calcd: C, 64.88; H, 7.49; N, 8.11; Cl, 10.26. Found: C, 64.64; H, 7.47; N, 7.94; Cl, 9.98.

Analytical HPLC (Method 1): >99%, $t_r$=24.1 min.

EXAMPLE 3

1-[N-(3-Chloroindole-6-carbonyl)-β-phenyl-D-alanyl]-4-(1-methylpiperidin-4-yl)piperidine Hydrochloride Prepared from 1-(β-phenyl-D-alanyl)-4-(1-methylpiperidin-4-yl)piperidine hydrochloride and 3-chloroindole-6-carboxylic acid using methods substantially equivalent to General Coupling Method 1. The HCl salt is prepared following Salt Formation Method 2.

$^1$H NMR.

ES-MS, m/z 507.3 (M+1)$^+$; 505.3 (M−1)$^−$.

Analysis For $C_{29}H_{35}ClN_4O_2 \cdot 1.1HCl \cdot 1.0H_2O$. Calcd: C, 61.63; H, 6.80; N, 9.91; Cl, 13.17. Found: C, 61.60; H, 6.58; N, 9.92; Cl, 13.50.

Analytical HPLC (Method 1): >99%, $t_r$=30.2 min.

EXAMPLE 4

1-[N-(5-Chloroindole-2-carbonyl)-β-phenyl-D-alanyl]-4-(1-methylpiperidin-4-yl)piperidine Hydrochloride Prepared from 1-β-phenyl-D-alanyl-4-(1-methylpiperidin-4-yl)piperidine hydrochloride and 5-chloroindole-2-carboxylic acid using methods substantially equivalent to General Coupling Method 1. The HCl salt is prepared following Salt Formation Method 2.

$^1$H NMR.

ES-MS, m/z 507.3 (M+1)$^+$; 505.3 (M−1)$^−$.

Analysis For $C_{29}H_{35}ClN_4O_2 \cdot 1.1HCl \cdot 1.0H_2O$. Calcd: C, 61.63; H, 6.80; N, 9.91; Cl, 13.17. Found: C, 61.15; H, 6.64; N, 9.63; Cl, 13.04.

Analytical HPLC (Method 1): >98%, $t_r$=34.3 min.

EXAMPLE 5

1-[N-(3-Methylindole-6-carbonyl)-β-phenyl-D-alanyl]-4-(1-methylpiperidin-4-yl)piperidine Hydrochloride Prepared from 1-(β-phenyl-D-alanyl)-4-(1-methylpiperidin-4-yl)piperidine hydrochloride and 3-methylindole-6-carboxylic acid using methods substantially equivalent to General Coupling Method 1. The HCl salt is prepared following Salt Formation Method 2.

$^1$H NMR.

ES-MS, m/z 487.4 (M+1)$^+$; 485.4 (M−1)$^−$.

Analysis For $C_{30}H_{38}N_4O_2 \cdot 1.15HCl \cdot 1.1H_2O$. Calcd: C, 65.70; H, 7.60; N, 10.21; Cl, 7.44. Found: C, 65.42; H, 7.32; N, 10.19; Cl, 7.33.

Analytical HPLC (Method 1): >96%, $t_r$=29.2 min.

EXAMPLE 6

1-[N-(4-Chlorobenzoyl)-β-phenyl-D-alanyl]-4-(1-methylpiperidin-4-yl)piperidine Hydrochloride Prepared from 1-(β-phenyl-D-alanyl)-4-(1-methylpiperidin-4-yl)piperidine hydrochloride and 4-chlorobenzoyl chloride using methods substantially equivalent to General Coupling Method 3. The HCl salt is prepared following Salt Formation Method 2.

$^1$H NMR.

ES-MS, m/z 468.4 (M+1)$^+$; 466.4 (M−1)$^−$.

Analysis For $C_{27}H_{34}ClN_3O_2 \cdot 1.0HCl \cdot 0.5H_2O$. Calcd: C, 64.09; H, 7.27; N, 8.30; Cl, 14.01. Found: C, 63.65; H, 7.07; N, 8.19; Cl, 13.93.

Analytical HPLC (Method 1): >97%, $t_r$=29.3 min.

EXAMPLE 7

1-[N-(Indole-6-carbonyl)-(γ-methyl)-D-glutamyl]-4-(1-methylpiperidin-4-yl)piperidine Hydrochloride Prepared from 1-[(γ-methyl)-D-glutamyl]-4-(1-methylpiperidin-4-yl)piperidine dihydrochloride and indole-6-carboxylic acid using methods substantially equivalent to General Coupling Method 1. The HCl salt is prepared following General Salt Formation Method 2.

$^1$H NMR.

ES-MS, m/z 469.5(M+1)$^+$; 467.5 (M−1)$^−$.

Analysis For $C_{26}H_{36}N_4O_4 \cdot 1HCl \cdot 1.0H_2O$. Calcd: C, 59.70; H, 7.52; N, 10.71. Found: C, 59.73; H, 7.49; N, 10.45.

Analytical HPLC (Method 1): >96%, $t_r$=16.6 min.

EXAMPLE 8

1-[N-(5-Chloroindole-2-carbonyl)-(γ-methyl)-D-glutamyl]-4-(1-methylpiperidin-4-yl)piperidine Hydrochloride Prepared from 1-[(γ-methyl)-D-glutamyl]-4-(1-methylpiperidin-4-yl)piperidine dihydrochloride and 5-chloroindole-2-carboxylic acid using methods substantially equivalent to General Coupling Method 1. The HCl salt is prepared following Salt Formation Method 2.
$^1$H NMR.
ES-MS, m/z 503.5 (M+1)$^+$; 501.5 (M−1)$^−$.
Analytical HPLC (Method 1): >96%, $t_r$=25.8 min.

EXAMPLE 9

1-[N-(Indole-6-carbonyl)-D-glutamyl]-4-(1-methylpiperidin-4-yl)piperidine Hydrochloride Prepared from 1-[(γ-methyl)-D-glutamyl]-4-(1-methylpiperidin-4-yl)piperidine dihydrochloride and indole-6-carboxylic acid using methods substantially equivalent to General Coupling Method 1. Ester deprotection with 2 eq LiOH and final purification and HCl salt formation via prep HPLC.
$^1$H NMR.
ES-MS, m/z 455.4 (M+1)$^+$; 453.5 (M−1)$^−$.
Analysis For $C_{25}H_{34}N_4O_4 \cdot 0.8HCl \cdot 3.5H_2O$. Calcd: C, 53.74; H, 7.40; N, 10.03; Cl, 5.08. Found: C, 53.20; H, 6.90; N, 9.90; Cl, 4.73.
Analytical HPLC (Method 1): >99%, $t_r$=13.0 min.

EXAMPLE 10

1-[N-(5-Chloroindole-2-carbonyl)-D-glutamyl]-4-(1-methylpiperidin-4-yl)piperidine Hydrochloride Prepared from 1-[(γ-methyl)-D-glutamyl]-4-(1-methylpiperidin-4-yl)piperidine dihydrochloride hydrochloride and 5-chloroindole-2-carboxylic acid using methods substantially equivalent to General Coupling Method 1. Ester deprotection with 2 eq LiOH and final purification and HCl salt formation via prep HPLC.
$^1$H NMR.
ES-MS, m/z 489.4 (M+1)$^+$; 487.4 (M−1)$^−$.
Analysis For $C_{25}H_{33}ClN_4O_4 \cdot 0.3HCl \cdot 1.7H_2O$. Calcd: C, 56.12; H, 6.86; N, 10.47; Cl, 8.61. Found: C, 55.67; H, 7.05; N, 10.51; Cl, 8.65.
Analytical HPLC (Method 1): >99%, $t_r$=23.2 min.

EXAMPLE 11

1-[N-(Indole-6-carbonyl)-D-aspartyl]-4-(1-methylpiperidin-4-yl)piperidine hydrochloride Prepared from 1-[(β-benzyl)-D-aspartyl]-4-(1-methylpiperidin-4-yl)piperidine Hydrochloride and indole-6-carboxylic acid using methods substantially equivalent to General Coupling Method 1. Ester deprotection with 2 eq LiOH and final purification and HCl salt formation via prep HPLC.
$^1$H NMR.
ES-MS, m/z 441.4(M+1)$^+$; 439.4 (M−1)$^−$.
Analytical HPLC (Method 1): >99%, $t_r$=12.3 min.

EXAMPLE 12a

1-[N-(Indole-6-carbonyl)-β-(3-pyridinyl)-D-alanyl]-4-(1-methylpiperidin-4-yl)piperidine Method D-1: To a solution of 1-[β-(3-pyridinyl)-D-alanyl]-4-(1-methylpiperidin-4-yl)piperidine trihydrochloride (0.850 g, 1.93 mmol) and indole-6-carboxylic acid (0.311 g, 1.93 mmol) in N,N-dimethylformamide (15 mL) under nitrogen atmosphere was added 1-hydroxybenzotriazole (0.261 g, 1.93 mmol) and N,N-diisopropylethylamine (0.749 g, 5.79 mmol) at 0° C. The mixture was stirred for 10 min at 0° C. then EDCI (0.408 g, 2.13 mmol) was added. The mixture was stirred for 16 h at room temperature. The mixture was diluted with water (100 mL) and washed four times with 50 mL portions of chloroform/2-propanol (3:1). The organic layer was washed with 50 mL portions of water and brine, dried over sodium sulfate, filtered, and concentrated under reduced pressure to give a crude oil. The oil was purified by flash chromatography, eluting with dichloromethane/CMA (50:1 to 3:1), to give the titled compound as a clear oil (0.250 g, 27%).
$^1$H NMR (CDCl$_3$).
APCI-MS, m/e=474 (M+1).

EXAMPLE 12b

1-[N-(Indole-6-carbonyl)-β-(3-pyridinyl)-D-alanyl]-4-(1-methylpiperidin-4-yl)piperidine Hydrochloride Salt Formation Method 3: To a solution of 1-[N-(indole-6-carbonyl)-β-(3-pyridinyl)-D-alanyl]-4-(1-methylpiperidin-4-yl)piperidine (0.370 g, 0.782 mmol) in acetonitrile (5 mL) at 0° C. was slowly added hydrochloric acid (1 M solution in diethyl ether, 0.782 mL, 0.782 mmol). The mixture was stirred for 10 minutes at 0° C. and was concentrated under reduced pressure to give the titled compound as an off-white solid (0.378 g, 95%).
$[\alpha]^{25}_D$+7.0° (c=0.5, Methanol).
Melting Point=177–182° C. with decomposition.
$^1$H NMR (CD$_3$OD).
APCI-MS, m/e=474 [$C_{28}H_{35}N_5O_2$+1].
Analysis for $C_{28}H_{35}N_5O_2 \cdot 1.1HCl \cdot 2.9H_2O$: Calcd: C, 59.42; H, 7.46; N, 12.12; Cl, 6.89. Found: C, 59.65; H, 7.46; N, 12.12; Cl, 7.01.
HPLC Analysis (Method A): 98.4% $t_r$=9.4 min.
TLC Analysis: $R_f$=0.27 (1:1 Dichloromethane/CMA).

EXAMPLE 13a

1-[N-(Indole-6-carbonyl)-β-(4-pyridinyl)-D-alanyl]-4-(1-methylpiperidin-4-yl)piperidine Using methods substantially equivalent to those described in Method D-1, the titled compound was prepared from 1-[β-(4-pyridinyl)-D-alanyl]-4-(1-methylpiperidin-4-yl)piperidine trihydrochloride and indole-6-carboxylic acid (23%).
$^1$H NMR (CDCl$_3$).
APCI-MS, m/e=474 (M+1).

EXAMPLE 13b

1-[N-(Indole-6-carbonyl)-β-(4-pyridinyl)-D-alanyl]-4-(1-methylpiperidin-4-yl)piperidine Hydrochloride Using methods substantially equivalent to those described in Salt Formation Method 3, the titled compound was prepared from 1-[N-(indole-6-carbonyl)-β-(4-pyridinyl)-D-alanyl]-4-(1-methylpiperidin-4-yl)piperidine (96%).
$[\alpha]^{25}_D$+16.0° (c 0.5, Methanol).
Melting Point=183–186° C. with decomposition.
$^1$H NMR (CD$_3$OD).
APCI-MS, m/e=474 [$C_{28}H_{35}N_5O_2$+1].
Analysis for $C_{28}H_{35}N_5O_2 \cdot 1.1HCl \cdot 2.5H_2O$: Calcd: C, 60.19; H, 7.41; N, 12.53; Cl, 6.98. Found: C, 60.54; H, 7.32; N, 12.59; Cl, 7.03.
HPLC Analysis (Method A): >99% $t_r$=8.7 min.
TLC Analysis: $R_f$=0.29 (1:1 Dichloromethane/CMA).

EXAMPLE 14a

1-[N-(Indole-6-carbonyl)-β-(2-pyridinyl)-D-alanyl]-4-(1-methylpiperidin-4-yl)piperidine Using methods substantially equivalent to those described in Method D-1, the subtitled compound was prepared from 1-[β-(2-pyridinyl)-D-alanyl]-4-(1-methylpiperidin-4-yl)piperidine trihydrochloride and indole-6-carboxylic acid (32%).
$^1$H NMR (CDCl$_3$).
APCI-MS, m/e=474 (M+1).

EXAMPLE 14b

1-[N-(Indole-6-carbonyl)-β-(2-pyridinyl)-D-alanyl]-4-(1-methylpiperidin-4-yl)piperidine Hydrochloride Using methods substantially equivalent to those described in Salt Formation Method 3, the titled compound was prepared from 1-[N-(indole-6-carbonyl)-β-(2-pyridinyl)-D-alanyl]-4-(1-methylpiperidin-4-yl)piperidine (95%).
$[\alpha]^{25}_D$+13.8° (c 0.5, Methanol).
Melting Point=175–179° C. with decomposition.
$^1$H NMR (CD$_3$OD).
APCI-MS, m/e=474 [C$_{28}$H$_{35}$N$_5$O$_2$+1].
Analysis for C$_{28}$H$_{35}$N$_5$O$_2$.1.1HCl.2.8H$_2$O: Calcd: C, 59.61; H, 7.45; N, 12.41; Cl, 6.91. Found: C, 59.47; H, 7.43; N, 12.28; Cl, 7.07.
HPLC Analysis (Method A): >99% t$_r$=8.9 min.
TLC Analysis: R$_f$=0.30 (1:1 Dichloromethane/CMA).

EXAMPLE 15a

1-[N-(Indole-6-carbonyl)-1-methyl-D-histidinyl]-4-(1-methylpiperidin-4-yl)piperidine Using methods substantially equivalent to those described in Method D-1, the subtitled compound was prepared from 1-(1-methyl-D-histidinyl)-4-(1-methylpiperidin-4-yl)piperidine trihydrochloride and indole-6-carboxylic acid (23%).
$^1$H NMR (CDCl$_3$).
APCI-MS, m/e 477 (C$_{27}$H$_{36}$N$_6$O$_2$+1).

EXAMPLE 15b

1-[N-(Indole-6-carbonyl)-1-methyl-D-histidinyl]-4-(1-methylpiperidin-4-yl)piperidine Hydrochloride Using methods substantially equivalent to those described in Salt Formation Method 3, the titled compound was prepared from 1-[N-(indole-6-carbonyl)-1-methyl-D-histidinyl]-4-(1-methylpiperidin-4-yl)piperidine (94%).
$[\alpha]^{25}_D$+46.7° (c 0.25, Methanol)
Melting Point=179–185° C. with decomposition.
$^1$H NMR (CD$_3$OD).
APCI-MS, m/e 477 (C$_{27}$H$_{36}$N$_6$O$_2$+1).
TLC R$_f$=0.67 (3:7 CH$_2$Cl$_2$:CMA)
Analysis for C$_{27}$H$_{36}$N$_6$O$_2$.1.6HCl.4.1H$_2$O: Calcd: C, 53.27; H, 7.58; N, 13.80; Cl, 9.32. Found: C, 53.47; H, 7.55; N, 13.58; Cl, 9.51.
HPLC Analysis (Method A): >99% t$_r$=9.6 min.

EXAMPLE 16a

1-[N-(Indole-6-carbonyl)-β-cyclohexyl-D-alanyl]-4-(1-methylpiperidin-4-yl)piperidine Using methods substantially equivalent to that described in Method D-1, the titled compound was prepared from 1-(β-cyclohexyl-D-alanyl)-4-(1-methylpiperidin-4-yl)piperidine dihydrochloride and indole-6-carboxylic acid (65%).
$^1$H NMR (CDCl$_3$).
TLC R$_f$=0.37 (5:2 CH$_2$Cl$_2$:CMA)

EXAMPLE 16b

1-[N-(Indole-6-carbonyl)-β-cyclohexyl-D-alanyl]-4-(1-methylpiperidin-4-yl)piperidine Hydrochloride Using methods substantially equivalent to those described in Salt Formation Method 3, the titled compound was prepared from 1-[N-(indole-6-carbonyl)-β-cyclohexyl-D-alanyl]-4-(1-methylpiperidin-4-yl)piperidine (96%).
$[\alpha]^{25}_D$–32.7° (c 0.20, Methanol)
Melting Point=162–172° C. with decomposition.
$^1$H NMR (CD$_3$OD).
APCI-MS, m/e=479 (C$_{29}$H$_{42}$N$_4$O$_2$+1).
TLC R$_f$=0.37 (5:2 CH$_2$Cl$_2$:CMA)
Analysis for C$_{29}$H$_{42}$N$_4$O$_2$.HCl.1.7H$_2$O: Calcd: C, 63.82; H, 8.57; N, 10.27; Cl, 6.50. Found: C, 63.66; H, 8.63; N, 10.26; Cl, 6.75.
HPLC Analysis (Method A): >99% t$_r$=15.8 min.

EXAMPLE 17a

1-[N-(Indole-6-carbonyl)-β-(4-tetrahydropyranyl)alanyl]-4-(1-methylpiperidin-4-yl)piperidine Using methods substantially equivalent to that described in Method D-1, the subtitled compound was prepared from 1-[β-(4-tetrahydropyranyl)alanyl]-4-(1-methylpiperidin-4-yl)piperidine dihydrochloride and indole-6-carboxylic acid (69%).
$^1$H NMR (CDCl$_3$).
TLC R$_f$=0.19 (5:2 CH$_2$Cl$_2$:CMA)

EXAMPLE 17b

1-[N-(Indole-6-carbonyl)-β-(4-tetrahydropyranyl)alanyl]-4-(1-methylpiperidin-4-yl)piperidine Hydrochloride Using methods substantially equivalent to those described in Salt Formation Method 3, the titled compound was prepared from 1-[N-(indole-6-carbonyl)-β-(4-tetrahydropyranyl)alanyl]-4-(1-methylpiperidin-4-yl)piperidine (96%).
Melting Point=162–178° C. with decomposition.
$^1$H NMR (CD$_3$OD).
APCI-MS, m/e=481 (C$_{28}$H$_{40}$N$_4$O$_3$+1).
TLC R$_f$=0.19 (5:2 CH$_2$Cl$_2$:CMA)
Analysis for C$_{28}$H$_{40}$N$_4$O$_3$.1.1HCl.2.5H$_2$O: Calcd: C, 59.44; H, 8.21; N, 9.90; Cl, 6.89. Found: C, 59.60; H, 8.38; N, 9.84; Cl, 6.74.
HPLC Analysis (Method A): >99% t$_r$=11.7 min.

EXAMPLE 18

1-[N-(6-Chlorobenzo[b]thiophene-2-carbonyl)-β-cyclohexyl-D-alanyl]-4-(1-methylpiperidin-4-yl)piperazine Hydrochloride Prepared from 1-(β-cyclohexyl-D-alanyl)-4-(1-methylpiperidin-4-yl)piperazine hydrochloride and 6-chlorobenzo[b]thiophene-2-carboxylic acid using methods substantially equivalent to General Coupling Method 1. The HCl salt is prepared following Salt Formation Method 1.
$^1$H NMR.
ES-MS, m/z 531.4 (M+1)$^+$; 529.4 (M−1)$^-$.
Analysis For $C_{28}H_{39}ClN_4O_2S.1.1HCl.4.0H_2O$. Calcd: C, 52.27; H, 7.54; N, 8.71. Found: C, 51.83; H, 6.58; N, 8.53.
Analytical HPLC (Method 1): >99%, $t_r$=32.6 min.

EXAMPLE 19

1-[N-(5-Chloroindole-2-carbonyl)-β-cyclohexyl-D-alanyl]-4-(1-methylpiperidin-4-yl)piperazine Hydrochloride Prepared from 1-(β-cyclohexyl-D-alanyl)-4-(1-methylpiperidin-4-yl)piperazine hydrochloride and 5-chloroindole-2-carboxylic acid using methods substantially equivalent to General Coupling Method 1. The HCl salt is prepared following Salt Formation Method 1.
$^1$H NMR.
ES-MS, m/z 514.2 (M+1)$^+$; 512.3 (M−1)$^-$.
Analysis For $C_{28}H_{40}ClN_5O_2.1.0HCl.3.5H_2O$. Calcd: C, 54.81; H, 7.89; N, 11.41. Found: C, 54.92; H, 6.93; N, 11.20.
Analytical HPLC (Method 1): >99%, $t_r$=31.6 min.

EXAMPLE 20

1-[N-(Indole-6-carbonyl)-β-cyclohexyl-D-alanyl]-4-(1-methylpiperidin-4-yl)piperazine Hydrochloride Prepared from 1-(β-cyclohexyl-D-alanyl)-4-(1-methylpiperidin-4-yl)piperazine hydrochloride and indole-6-carboxylic acid using methods substantially equivalent to General Coupling Method 1. The HCl salt is prepared following General Salt Formation Method 1.
$^1$H NMR.
ES-MS, m/z 480.3 (M+1)$^+$; 478.3 (M−1)$^-$.
Analysis For $C_{28}H_{41}N_5O_2.1.1HCl.3.5H_2O$. Calcd: C, 57.70; H, 8.49; N, 12.02. Found: C, 57.39; H, 7.89; N, 11.78.
Analytical HPLC (Method 1): >99%, $t_r$=25.1 min.

EXAMPLE 21

1-[N-(6-Chlorobenzo[b]thiophene-2-carbonyl)-β-(4-tetrahydropyranyl)alanyl]-4-(1-methylpiperidin-4-yl)piperazine Hydrochloride Prepared from 1-[β-(4-tetrahydropyranyl)alanyl]-4-(1-methylpiperidin-4-yl)piperazine hydrochloride and 6-chlorobenzo[b]thiophene-2-carboxylic acid using methods substantially equivalent to General Coupling Method 1. The HCl salt is prepared following Salt Formation Method 1.
$^1$H NMR.
ES-MS, m/z 533.2 (M+1)$^+$; 531.3 (M−1)$^-$.
Analysis For $C_{27}H_{37}ClN_4O_3S.1.0HCl.2.0H_2O$. Calcd: C, 53.55; H, 6.99; N, 9.25. Found: C, 53.16; H, 6.46; N, 9.34.
Analytical HPLC (Method 1): >99%, $t_r$=24.1 min.

EXAMPLE 22

1-[N-(5-Chloroindole-2-carbonyl)-β-(4-tetrahydropyranyl)alanyl]-4-(1-methylpiperidin-4-yl)piperazine Hydrochloride Prepared from 1-[β-(4-tetrahydropyranyl)alanyl]-4-(1-methylpiperidin-4-yl)piperazine hydrochloride and 5-chloroindole-2-carboxylic acid using methods substantially equivalent to General Coupling Method 1. The HCl salt is prepared following Salt Formation Method 1.
$^1$H NMR.
ES-MS, m/z 516.2 (M+1)$^+$; 514.3 (M−1)$^-$.
Analysis For $C_{25}H_{36}N_4O_2.1.1HCl.2.0H_2O$. Calcd: C, 54.09; H, 7.28; N, 11.68. Found: C, 54.34; H, 6.83; N, 11.69.
Analytical HPLC (Method 1): >97%, $t_r$=23.2 min.

EXAMPLE 23

1-[N-(Indole-6-carbonyl)-β-(4-tetrahydropyranyl)alanyl]-4-(1-methylpiperidin-4-yl)piperazine Hydrochloride Prepared from 1-[β-(4-tetrahydropyranyl)alanyl]-4-(1-methylpiperidin-4-yl)piperazine hydrochloride and indole-2-carboxylic acid using methods substantially equivalent to General Coupling Method 1. The HCl salt is prepared following General Salt Formation Method 1.
$^1$H NMR.
ES-MS, m/z 482.3 (M+1)$^+$; 480.3 (M−1)$^-$.
Analysis For $C_{27}H_{39}N_5O_3.1.1HCl.3.5H_2O$. Calcd: C, 55.45; H, 8.12; N, 11.98. Found: C, 55.20; H, 7.06; N, 11.94.
Analytical HPLC (Method 1): >99%, $t_r$=15.5 min.

EXAMPLE 24a

1-[N-(Indole-6-carbonyl)-β-(4-pyridinyl)-D-alanyl]-4-(1-methylpiperidin-4-yl)piperazine Using methods substantially equivalent to those described in Method D-1, the titled compound was prepared from 1-[β-(4-pyridinyl)-D-alanyl]-4-(1-methylpiperidin-4-yl)piperazine tetrahydrochloride and indole-6-carboxylic acid (50%).
$^1$H NMR (CDCl$_3$).
APCI-MS, m/e=475 (M+1).

EXAMPLE 24b

1-[N-(Indole-6-carbonyl)-β-(4-pyridinyl)-D-alanyl]-4-(1-methylpiperidin-4-yl)piperazine Hydrochloride Using methods substantially equivalent to those described in Salt Formation Method 3, the titled compound was prepared from 1-[N-(indole-6-carbonyl)-β-(4-pyridinyl)-D-alanyl]-4-(1-methylpiperidin-4-yl)piperazine (96%).
$[α]^{25}_D$+25.0° (c 0.4, Methanol).
Melting Point=228–235° C. with decomposition.
$^1$H NMR (CD$_3$OD).
APCI-MS, m/e=475 $[C_{27}H_{34}N_6O_2+1]$.
Analysis for $C_{27}H_{34}N_6O_2.1.5HCl.2.2H_2O.0.1CH_2Cl_2$: Calcd: C, 56.37; H, 7.00; N, 14.55; Cl, 10.44. Found: C, 56.71; H, 7.01; N, 14.15; Cl, 10.25.
HPLC Analysis (Method A): >99% $t_r$=8.1 min.
TLC Analysis: $R_f$=0.36 (1:1 Dichloromethane/CMA).

EXAMPLE 25a

1-[N-(6-Chlorobenzo[b]thiophene-2-carbonyl)-β-(4-pyridinyl)-D-alanyl]-4-(1-methylpiperidin-4-yl)piperazine Using methods substantially equivalent to those described in Method D-1, the titled compound was prepared from 1-[β-(4-pyridinyl)-D-alanyl]-4-(1-methylpiperidin-4-yl)piperazine tetrahydrochloride and 6-chlorobenzo[b]thiophene-2-carboxylic acid (49%).
$^1$H NMR (CDCl$_3$).
APCI-MS, m/e=527 (M+1).

EXAMPLE 25b

1-[N-(6-Chlorobenzo[b]thiophene-2-carbonyl)-β-(4-pyridinyl)-D-alanyl]-4-(1-methylpiperidin-4-yl)piperazine Hydrochloride Using methods substantially equivalent to those described in Salt Formation Method 3, the titled compound was prepared from 1-[N-(6-chlorobenzo[b]thiophene-2-carbonyl)-β-(4-pyridinyl)-D-alanyl]-4-(1-methylpiperidin-4-yl)piperazine (94%).
$[\alpha]^{25}_D$+7.4° (c 0.05, Methanol).
Melting Point=213–217° C. with decomposition.
$^1$H NMR (CD$_3$OD).
APCI-MS, m/e=527 [C$_{27}$H$_{32}$ClN$_5$O$_2$S+1].
Analysis for C$_{27}$H$_{32}$ClN$_5$O$_2$S.1.9HCl.1.4H$_2$O: Calcd: C, 52.26; H, 5.96; N, 11.29; Cl, 16.57. Found: C, 52.41; H, 6.07; N, 11.08; Cl, 16.77.
HPLC Analysis (Method A): >99% t$_r$=9.4 min.
TLC Analysis: R$_f$=0.46 (1:1 Dichloromethane/CMA).

EXAMPLE 26a

1-[N-(5-Chloroindole-2-carbonyl)-β-(4-pyridinyl)-D-alanyl]-4-(1-methylpiperidin-4-yl)piperazine Using methods substantially equivalent to those described in Method D-1, the titled compound was prepared from 1-[β-(4-pyridinyl)-D-alanyl]-4-(1-methylpiperidin-4-yl)piperazine tetrahydrochloride and 5-chloroindole-2-carboxylic acid (47%).
$^1$H NMR (CDCl$_3$).
APCI-MS, m/e=510 (M+1).

EXAMPLE 26b

1-[N-(5-Chloroindole-2-carbonyl)-β-(4-pyridinyl)-D-alanyl]-4-(1-methylpiperidin-4-yl)piperazine Hydrochloride Using methods substantially equivalent to those described in Salt Formation Method 3, the titled compound was prepared from 1-[N-(5-chloroindole-2-carbonyl)-β-(4-pyridinyl)-D-alanyl]-4-(1-methylpiperidin-4-yl)piperazine (94%).
$[\alpha]^{25}_D$+30.6° (c 0.17, Methanol).
Melting Point=238–242° C. with decomposition.
$^1$H NMR (CD$_3$OD).
APCI-MS, m/e=509 [C$_{27}$H$_{33}$ClN$_6$O$_2$+1].
Analysis for C$_{27}$H$_{33}$ClN$_6$O$_2$.2.2HCl.1.8H$_2$O: Calcd: C, 52.16; H, 6.29; N, 13.52; Cl, 18.25. Found: C, 52.26; H, 6.12; N, 13.28; Cl, 18.23.
HPLC Analysis (Method A): >99% t$_r$=10.9 min.
TLC Analysis: R$_f$=0.33 (1:1 Dichloromethane/CMA).

EXAMPLE 27a

1-[N-(6-Chlorobenzo[b]thiophene-2-carbonyl)-β-(2-pyridinyl)-D-alanyl]-4-(1-methylpiperidin-4-yl)piperazine Using methods substantially equivalent to those described in Method D-1, the titled compound was prepared from 1-[β-(2-pyridinyl)-D-alanyl]-4-(1-methylpiperidin-4-yl)piperazine tetrahydrochloride and 6-chlorobenzo[b]thiophene-2-carboxylic acid (53%).
$^1$H NMR (CDCl$_3$).
APCI-MS, m/e=427 (M+1).

EXAMPLE 27b

1-[N-(6-Chlorobenzo[b]thiophene-2-carbonyl)-β-(2-pyridinyl)-D-alanyl]-4-(1-methylpiperidin-4-yl)piperazine Hydrochloride Using methods substantially equivalent to those described in Salt Formation Method 3, the titled compound was prepared from 1-[N-(6-chlorobenzo[b]thiophene-2-carbonyl)-β-(2-pyridinyl)-D-alanyl]-4-(1-methylpiperidin-4-yl)piperazine (96%).
$[\alpha]^{25}_D$+7.4° (c 0.05, Methanol).
Melting Point=219–223° C. with decomposition.
$^1$H NMR (CD$_3$OD).
APCI-MS, m/e=526 [C$_{27}$H$_{32}$ClN$_5$O$_2$S+1].
Analysis for C$_{27}$H$_{32}$ClN$_5$O$_2$S.1.4HCl.1.75H$_2$O: Calcd: C, 53.28; H, 6.11; N, 11.51; Cl, 13.98. Found: C, 53.50; H, 6.03; N, 11.30; Cl, 13.86.
HPLC Analysis (Method A): 98.9% t$_r$=9.9 min.
TLC Analysis: R$_f$=0.46 (1:1 Dichloromethane/CMA).

EXAMPLE 28a

1-[N-(Indole-6-carbonyl)-β-(2-pyridinyl)-D-alanyl]-4-(1-methylpiperidin-4-yl)piperazine Using methods substantially equivalent to those described in Method D-1, the titled compound was prepared from 1-[β-(2-pyridinyl)-D-alanyl]-4-(1-methylpiperidin-4-yl)piperazine tetrahydrochloride and indole-6-carboxylic acid (62%).
$^1$H NMR (CDCl$_3$).
APCI-MS, m/e=475 (M+1).

EXAMPLE 28b

1-[N-(Indole-6-carbonyl)-β-(2-pyridinyl)-D-alanyl]-4-(1-methylpiperidin-4-yl)piperazine Hydrochloride Using methods substantially equivalent to those described in Salt Formation Method 3, the titled compound was prepared from 1-[N-(indole-6-carbonyl)-β-(2-pyridinyl)-D-alanyl]-4-(1-methylpiperidin-4-yl)piperazine (94%).
$[\alpha]^{25}_D$+2.3° (c 0.05, Methanol).
Melting Point=232–235° C. with decomposition.
$^1$H NMR (CD$_3$OD).
APCI-MS, m/e=475 [C$_{27}$H$_{34}$N$_6$O$_2$+1].
Analysis for C$_{27}$H$_{34}$N$_6$O$_2$.1.75HCl.3.9H$_2$O: Calcd: C, 53.28; H, 7.21; N, 13.81; Cl, 10.19. Found: C, 53.33; H, 7.18; N, 13.70; Cl, 10.26.
HPLC Analysis (Method A): 98.5% t$_r$=6.9 min.
TLC Analysis: R$_f$=0.32 (1:1 Dichloromethane/CMA).

EXAMPLE 29a

1-[N-(5-Chloroindole-2-carbonyl)-β-(2-pyridinyl)-D-alanyl]-4-(1-methylpiperidin-4-yl)piperazine Using methods substantially equivalent to those described in Method D-1, the subtitled compound was prepared from 1-[β-(2-pyridinyl)-D-alanyl]-4-(1-methylpiperidin-4-yl)piperazine tetrahydrochloride and 5-chloroindole-2-carboxylic acid (54%).

$^1$H NMR (CDCl$_3$).
APCI-MS, m/e=510 (M+1).

EXAMPLE 29b

1-[N-(5-Chloroindole-2-carbonyl)-β-(2-pyridinyl)-D-alanyl]-4-(1-methylpiperidin-4-yl)piperazine Hydrochloride Using methods substantially equivalent to those described in Salt Formation Method 3, the titled compound was prepared from 1-[N-(5-chloroindole-2-carbonyl)-β-(2-pyridinyl)-D-alanyl]-4-(1-methylpiperidin-4-yl)piperazine (94%).

Melting Point=210–214° C. with decomposition.
$^1$H NMR (CD$_3$OD).
APCI-MS, m/e=509 [C$_{27}$H$_{33}$ClN$_6$O$_2$+1].
Analysis for C$_{27}$H$_{33}$ClN$_6$O$_2$.2.25HCl.1.2H$_2$O: Calcd: C, 52.93; H, 6.19; N, 13.72; Cl, 18.81. Found: C, 52.06; H, 6.12; N, 13.51; Cl, 18.67.
HPLC Analysis (Method A): >99% t$_r$=10.9 min.
TLC Analysis: R$_f$=0.38 (1:1 Dichloromethane/CMA).

EXAMPLE 30a

1-[N-(Indole-6-carbonyl)-D-glutamyl]-4-(1-methylpiperidin-4-yl)piperazine

Using methods substantially equivalent to those described in Method D-1, the titled compound was prepared from 1-(D-glutamyl)-4-(1-methylpiperidin-4-yl)piperazine trihydrochloride and indole-6-carboxylic acid (46%).

$^1$H NMR (CDCl$_3$).
APCI-MS, m/e=455 (M+1).

EXAMPLE 30b

1-[N-(Indole-6-carbonyl)-D-glutamyl]-4-(1-methylpiperidin-4-yl)piperazine Hydrochloride Using methods substantially equivalent to those described in Salt Formation Method 3, the titled compound was prepared from 1-[N-(indole-6-carbonyl)-D-glutamyl]-4-(1-methylpiperidin-4-yl)piperazine (96%).

Melting Point=215–218° C. with decomposition.
$^1$H NMR (CD$_3$OD).
APCI-MS, m/e=455 [C$_{24}$H$_{34}$N$_6$O$_3$+1].
Analysis for C$_{24}$H$_{34}$N$_6$O$_3$.2.0HCl.3.1H$_2$O: Calcd: C, 49.42; H, 7.21; N, 14.41; Cl, 12.16. Found: C, 49.67; H, 7.43; N, 14.13; Cl, 11.89.
HPLC Analysis (Method A): >99% t$_r$=14.7 min.
TLC Analysis: R$_f$=0.32 (CMA).

EXAMPLE 31a

1-[N-(6-Chlorobenzo[b]thiophene-2-carbonyl)-D-glutamyl]-4-(1-methylpiperidin-4-yl)piperazine Using methods substantially equivalent to those described in Method D-1, the subtitled compound was prepared from 1-(D-glutamyl)-4-(1-methylpiperidin-4-yl)piperazine trihydrochloride and 6-chlorobenzo[b]thiophene-2-carboxylic acid (41%).

$^1$H NMR (CDCl$_3$).
APCI-MS, m/e=507 (M+1).

EXAMPLE 31b

1-[N-(6-Chlorobenzo[b]thiophene-2-carbonyl)-D-glutamyl]-4-(1-methylpiperidin-4-yl)piperazine Hydrochloride Using methods substantially equivalent to those described in Salt Formation Method 3, the titled compound was prepared from 1-[N-(6-chlorobenzo[b]thiophene-2-carbonyl)-D-glutamyl]-4-(1-methylpiperidin-4-yl)piperazine (93%).

Melting Point=185–190° C. with decomposition.
$^1$H NMR (CD$_3$OD).
APCI-MS, m/e=506 [C$_{24}$H$_{32}$ClN$_5$O$_3$S+1].
Analysis for C$_{24}$H$_{32}$ClN$_5$O$_3$S.1.4HCl.2.6H$_2$O: Calcd: C, 47.73; H, 6.44; N, 11.60; Cl, 14.09. Found: C, 47.58; H, 6.37; N, 11.52; Cl, 14.07.
HPLC Analysis (Method A): >99% t$_r$=11.9 min.
TLC Analysis: R$_f$=0.34 (CMA).

EXAMPLE 32a

1-[N-(5-Chloroindole-2-carbonyl)-D-glutamyl]-4-(1-methylpiperidin-4-yl)piperazine Using methods substantially equivalent to those described in Method D-1, the titled compound was prepared from 1-(D-glutamyl)-4-(1-methylpiperidin-4-yl)piperazine trihydrochloride and 5-chloroindole-2-carboxylic acid (43%).

$^1$H NMR (CDCl$_3$).
APCI-MS, m/e=489 (M+1).

EXAMPLE 32b

1-[N-(5-Chloroindole-2-carbonyl)-D-glutamyl]-4-(1-methylpiperidin-4-yl)piperazine Hydrochloride Using methods substantially equivalent to those described in Salt Formation Method 3, the titled compound was prepared from 1-[N-(5-chloroindole-2-carbonyl)-D-glutamyl]-4-(1-methylpiperidin-4-yl)piperazine (96%).

Melting Point=222–225° C. with decomposition.
$^1$H NMR (CD$_3$OD).
APCI-MS, m/e=489 [C$_{24}$H$_{33}$ClN$_6$O$_3$+1].
Analysis for C$_{24}$H$_{33}$ClN$_6$O$_3$.2.0HCl.2.3H$_2$O: Calcd: C, 47.78; H, 6.61; N, 13.93; Cl, 17.63. Found: C, 47.99; H, 6.86; N, 13.57; Cl, 17.60.
HPLC Analysis (Method A): 95.2% t$_r$=11.4 min.
TLC Analysis: R$_f$=0.23 (CMA).

EXAMPLE 33a

1-[N-(6-Chlorobenzo[b]thiophene-2-carbonyl)-β-(1-methylpiperidin-4-yl)-D-alanyl]-4-(1-methylpiperidin-4-yl)piperazine Using methods substantially equivalent to those described in Method D-1, the titled compound was prepared from 1-[β-(1-methylpiperidin-4-yl)-D-alanyl]-4-(1-methylpiperidin-4-yl)piperazine tetrahydrochloride and 6-chlorobenzo[b]thiophene-2-carboxylic acid (52%).
$^1$H NMR (CDCl$_3$).
APCI-MS, m/e=547 (M+1).

EXAMPLE 33b

1-[N-(6-Chlorobenzo[b]thiophene-2-carbonyl)-β-(1-methylpiperidin-4-yl)-D-alanyl]-4-(1-methylpiperidin-4-yl)piperazine Hydrochloride Using methods substantially equivalent to those described in Salt Formation Method 3, the subtitled compound was prepared from 1-[N-(6-chlorobenzo[b]thiophene-2-carbonyl)-β-(1-methylpiperidin-4-yl)-D-alanyl]-4-(1-methylpiperidin-4-yl)piperazine (96%).
Melting Point=220–223° C. with decomposition.
$^1$H NMR (CD$_3$OD).
APCI-MS, m/e=547 [C$_{28}$H$_{40}$ClN$_5$O$_2$S+1].
Analysis for C$_{28}$H$_{40}$ClN$_5$O$_2$S.2.4HCl.2.0H$_2$O: Calcd: C, 50.22; H, 6.98; N, 10.46; Cl, 18.00. Found: C, 49.96; H, 6.79; N, 10.34; Cl, 18.13.
HPLC Analysis (Method A): 97.5% t$_r$=11.2 min.
TLC Analysis: R$_f$=0.34 (CMA).

EXAMPLE 34a

1-[N-(Indole-6-carbonyl)-β-(1-methylpiperidin-4-yl)-D-alanyl]-4-(1-methylpiperidin-4-yl)piperazine Using methods substantially equivalent to those described in Method D-1, the subtitled compound was prepared from 1-[β-(1-methylpiperidin-4-yl)-D-alanyl]-4-(1-methylpiperidin-4-yl)piperazine tetrahydrochloride and indole-6-carboxylic acid (59%).
$^1$H NMR (CDCl$_3$).
APCI-MS, m/e=495 (M+1).

EXAMPLE 34b

1-[N-(Indole-6-carbonyl)-β-(1-methylpiperidin-4-yl)-D-alanyl]-4-(1-methylpiperidin-4-yl)piperazine Hydrochloride Using methods substantially equivalent to those described in Salt Formation Method 3, the titled compound was prepared from 1-[N-(indole-6-carbonyl)-β-(1-methylpiperidin-4-yl)-D-alanyl]-4-(1-methylpiperidin-4-yl)piperazine (98%).
Melting Point=190–193° C. with decomposition.
$^1$H NMR (CD$_3$OD).
APCI-MS, m/e=495 [C$_{28}$H$_{42}$N$_6$O$_2$+1].
Analysis for C$_{28}$H$_{42}$N$_6$O$_2$.1.7HCl.1.8H$_2$O: Calcd: C, 57.09; H, 8.09; N, 14.27; Cl, 10.23. Found: C, 57.27; H, 8.41; N, 14.05; Cl, 10.20.
HPLC Analysis (Method A): 98.7% t$_r$=8.4 min.
TLC Analysis: R$_f$=0.33 (CMA).

EXAMPLE 35a

1-[N-(5-Chloroindole-2-carbonyl)-β-(1-methylpiperidin-4-yl)-D-alanyl]-4-(1-methylpiperidin-4-yl)piperazine Using methods substantially equivalent to those described in Method D-1, the titled compound was prepared from 1-[β-(1-methylpiperidin-4-yl)-D-alanyl]-4-(1-methylpiperidin-4-yl)piperazine tetrahydrochloride and 5-chloroindole-2-carboxylic acid (46%).
$^1$H NMR (CDCl$_3$).
APCI-MS, m/e=529 (M+1).

EXAMPLE 35b

1-[N-(5-Chloroindole-2-carbonyl)-β-(1-methylpiperidin-4-yl)-D-alanyl]-4-(1-methylpiperidin-4-yl)piperazine Hydrochloride Using methods substantially equivalent to those described in Salt Formation Method 3, the titled compound was prepared from 1-[N-(5-chloroindole-2-carbonyl)-β-(1-methylpiperidin-4-yl)-D-alanyl]-4-(1-methylpiperidin-4-yl)piperazine (96%).
Melting Point=205–210° C. with decomposition.
$^1$H NMR (CD$_3$OD).
APCI-MS, m/e=529 [C$_{28}$H$_{41}$ClN$_6$O$_2$+1].
Analysis for C$_{28}$H$_{41}$ClN$_6$O$_2$.1.5HCl.1.7H$_2$O: Calcd: C, 54.24; H, 7.53; N, 13.68; Cl, 14.42. Found: C, 54.48; H, 7.21; N, 13.54; Cl, 14.22.
HPLC Analysis (Method A): 96.6% t$_r$=10.9 min.
TLC Analysis: R$_f$=0.35 (CMA).

EXAMPLE 36a

1-[N-(Indole-6-carbonyl)-D-asparaginyl]-4-(1-methylpiperidin-4-yl)piperazine

Using methods substantially equivalent to those described in Method D-1, the titled compound was prepared from 1-(D-asparaginyl)-4-(1-methylpiperidin-4-yl)piperazine trihydrochloride and indole-6-carboxylic acid (45%).
$^1$H NMR (CDCl$_3$).
APCI-MS, m/e=451 (M+1).

EXAMPLE 36b

1-[N-(Indole-6-carbonyl)-D-asparaginyl]-4-(1-methylpiperidin-4-yl)piperazine Hydrochloride Using methods substantially equivalent to those described in Salt Formation Method 3, the titled compound was prepared from 1-[N-(indole-6-carbonyl)-D-asparaginyl]-4-(1-methylpiperidin-4-yl)piperazine (95%).
Melting Point=215–219° C. with decomposition.
$^1$H NMR (CD$_3$OD).
APCI-MS, m/e=441 [C$_{23}$H$_{32}$N$_6$O$_3$+1].
Analysis for C$_{23}$H$_{32}$N$_6$O$_3$.1.5HCl.3.0H$_2$O: Calcd: C, 50.29; H, 7.25; N, 15.30; Cl, 9.68. Found: C, 50.53; H, 7.14; N, 15.00; Cl, 9.68.
HPLC Analysis (Method A): 96.2% t$_r$=8.7 min.
TLC Analysis: R$_f$=0.21 (CMA).

EXAMPLE 37a

1-[N-(6-Chlorobenzo[b]thiophene-2-carbonyl)-D-asparaginyl]-4-(1-methylpiperidin-4-yl)piperazine Using methods substantially equivalent to those described in Method D-1, the subtitled compound was prepared from 1-(D-asparaginyl)-4-(1-methylpiperidin-4-yl)piperazine trihydrochloride and 6-chlorobenzo[b]thiophene-2-carboxylic acid (40%).

$^1$H NMR (CDCl$_3$).

APCI-MS, m/e=493 (M+1).

EXAMPLE 37b

1-[N-(6-Chlorobenzo[b]thiophene-2-carbonyl)-D-asparaginyl]-4-(1-methylpiperidin-4-yl)piperazine Hydrochloride Using methods substantially equivalent to those described in Salt Formation Method 3, the subtitled compound was prepared from 1-[N-(6-chlorobenzo[b]thiophene-2-carbonyl)-D-asparaginyl]-4-(1-methylpiperidin-4-yl)piperazine (98%).

Melting Point=219–223° C. with decomposition.

$^1$H NMR (CD$_3$OD).

APCI-MS, m/e=493 [C$_{23}$H$_{30}$ClN$_5$O$_3$S+1].

Analysis for C$_{23}$H$_{30}$ClN$_5$O$_3$S.1.4HCl.2.6H$_2$O: Calcd: C, 47.25; H, 6.05; N, 11.98; Cl, 16.37. Found: C, 47.13; H, 5.86; N, 11.88; Cl, 16.29.

HPLC Analysis (Method A): 95.9% t$_r$=11.7 min.

TLC Analysis: R$_f$=0.29 (CMA).

EXAMPLE 38a

1-[N-(5-Chloroindole-2-carbonyl)-D-asparaginyl])-4-(1-methylpiperidin-4-yl)piperazine Using methods substantially equivalent to those described in Method D-1, the subtitled compound was prepared from 1-[D-asparaginyl]-4-(1-methylpiperidin-4-yl)piperazine trihydrochloride and 5-chloroindole-2-carboxylic acid (46%).

$^1$H NMR (CDCl$_3$).

APCI-MS, m/e=475 (M+1).

EXAMPLE 38b

1-[N-(5-Chloroindole-2-carbonyl)-D-asparaginyl]-4-(1-methylpiperidin-4-yl)piperazine Hydrochloride Using methods substantially equivalent to those described in Salt Formation Method 3, the subtitled compound was prepared from 1-[N-(5-chloroindole-2-carbonyl)-D-asparaginyl]-4-(1-methylpiperidin-4-yl)piperazine (98%).

Melting Point=235–240° C. with decomposition.

$^1$H NMR (CD$_3$OD).

APCI-MS, m/e=475 [C$_{23}$H$_{31}$ClN$_6$O$_3$+1].

Analysis for C$_{23}$H$_{31}$ClN$_6$O$_3$.HCl.H$_2$O: Calcd: C, 47.25; H, 6.05; N, 11.98; Cl, 16.37. Found: C, 47.13; H, 5.86; N, 11.88; Cl, 16.29.

HPLC Analysis (Method A): >99% t$_r$=11.8 min.

TLC Analysis: R$_f$=0.25 (CMA).

EXAMPLE 39

1-[N-(Indole-6-carbonyl)-β-(trifluoromethyl)-D/L-alanyl]-4-(1-methylpiperidin-4-yl)piperazine Hydrochloride 1-(D,L-trifluoromethylalaninyl)-4-(1-methylpiperidin-4-yl)piperazine (330 mg), indole-6-carboxylic acid (200 mg), HOAt (180 mg), EDCI (260 mg) and triethylamine (0.5 ml) were dissolved in DMF and stirred overnight. All volatiles were removed under high vacuum and the residue partitioned between sat. aqueous sodium bicarbonate and 4:1 chloroform/isopropyl alcohol. The organic solution was washed with brine and dried (MgSO$_4$) and concentrated. The product thus obtained was purified by reverse phase HPLC and converted to the free base by absorption onto an SCX ion exchange column and elution with a solution of ammonia in methanol to give 1-(indole-6-carbonyl-D,L-trifluoromethylalaninyl)-4-(1-methylpiperidin-4-yl)piperazine (279 mg).

$^1$H NMR

LCMS m/z 466 (M+1)$^+$

Analytical HPLC Luna C$_{18}$ 3□m (4.6×30 mm column), linear gradient 18% to 90% acetonitrile in water with 0.1% TFA over 5 min: >95% t$_r$=1.99 min

EXAMPLE 40

1-[N-(5-Chloroindole-2-carbonyl)-β-(trifluoromethyl)-D/L-alanyl]-4-(1-methylpiperidin-4-yl)piperazine Hydrochloride Prepared from 1-(D,L-trifluoromethylalaninyl)-4-(1-methylpiperidiny-4-yl)piperazine and 5-chloroindole-2-carboxylic acid using methods substantially equivalent to that described above for 1-(indole-6-carbonyl-D,L-trifluoromethylalaninyl)-4-(1-methylpiperidin-4-yl)piperazine.

$^1$H NMR

LCMS m/z 500 (M+1)$^+$

Analytical HPLC Luna C$_{18}$ 3□m (4.6×30 mm column), linear gradient 18% to 90% acetonitrile in water with 0.1% TFA over 5 min: >95% t$_r$=2.51 min Enzyme Inhibition Assays:

The ability of a test compound to inhibit factor Xa may be evaluated in one or more of the following Enzyme Inhibition assays, or in other standard assays known to those skilled in the art.

Enzyme Inhibition Assay

Human factor Xa and human thrombin are purchased from Enzyme Research Laboratories (South Bend, Ind., USA). Other proteases are from other commercial sources. Chromogenic para-nitroanilide peptide protease substrates are purchased from Midwest Biotech (Fishers, Ind., USA).

The binding affinities for human factor Xa are measured as apparent association constants (Kass) derived from protease inhibition kinetics as described previously.[a,b,c,d] The apparent Kass values are obtained using automated (BioMek-1000) dilutions of inhibitors (Kass determinations are performed in triplicate at each of four-eight inhibitor concentrations) into 96-well plates and chromogenic substrate hydrolysis rates determined at 405 nm using a Thermomax plate reader from Molecular Devices (San Francisco). For factor Xa inhibition, the assay protocol is: 50 μL buffer (0.06 M tris, 0.3 M NaCl, pH 7.4); 25 μL inhibitor test solution (in MeOH); 25 μL human factor Xa (32 nM in 0.03 M tris, 0.15 M NaCl, 1 mg/mL HSA); finally, 150 μL BzIleGluGlyArgpNA (0.3 mM in water) added within 2 min to start hydrolysis. Final [factor Xa] is 3.2 nM. [Free Xa] and

[bound Xa] are determined from linear standard curves on the same plate by use of SoftmaxPro software for each inhibitor concentration and apparent Kass calculated for each inhibitor concentration which produced hydrolysis inhibition between 20% and 80% of the control (3.2 nM factor Xa): apparent Kass=[E:I]/[$E_f$][$I_f$]=[$E_b$]/[$E_f$][$I°-I_b$]. The apparent Kass values so obtained are approximately the inverse of the Ki for the respective inhibitors [1/appKass=app Ki]. The variability of mean apparent Kass values determined at the single substrate concentration is +/−15%. The assay system Km was measured as 0.347+/−0.031 mM [n=4]; and Vmax was 13.11+/−0.76 µM/min.

Kass values are determined with thrombin and other proteases using the same protocol with the following enzyme and substrate concentrations:
thrombin, 5.9 nM with 0.2 mM BzPheValArgpNA;
factor XIa, 1.2 nM with 0.4 mM pyroGluProArgpNA;
factor XIIa, 10 nM with 0.2 mM HDProPheArgpNA;
plasmin, 3.4 nM with 0.5 mM HDValLeuLyspNA;
nt-PA, 1.2 nM with 0.8 mM HDIleProArgpNA;
urokinase, 0.4 nM with 0.4 mM pyroGluGlyArgpNA;
aPC, 3 nM with 0.174 mM pyroGluProArgpNA;
plasma kallikrein, 1.9 nM with D-ProPheArgpNA; and
bovine trypsin, 1.4 nM with 0.18 mM BzPheValArgpNA.

Citations
(a) Sall D J, J A Bastian, S L Briggs, J A Buben, N Y Chirgadze, D K Clawson, M L Denny, D D Giera, D S Gifford-Moore, R W Harper, K L Hauser, V J Klimkowski, T J Kohn, H-S Lin, J R McCowan, A D Palkowitz, G F Smith, M E Richett, K Takeuchi, K J Thrasher, J M Tinsley, B G Utterback, S-CB Yan, M Zhang. Dibasic Benzo[b]thiophenes Derivatives as a Novel Class of Active Site Directed Thrombin Inhibitors. 1. Determination of the Serine Protease Selectivity, Structure-Activity Relationships and Binding Orientation. J Med Chem 40 3489–3493 (1997).
(b) Smith G F, T J Craft, D S Gifford-Moore, W J Coffman, K D Kurz, E Roberts, R T Shuman, G E Sandusky, N D Jones, N Chirgadze, and C V Jackson. A Family of Arginal Thrombin Inhibitors Related to Efegatran. Sem. Thrombos. Hemost. 22, 173–183 (1996).
(c) Smith G F, D S Gifford-Moore, T J Craft, N Chirgadze, K J Ruterbories, T D Lindstrom, J H Satterwhite. Efegatran: A New Cardiovascular Anticosagulant. In New Anticoagulants for the Cardiovascular Patient. Ed. R Pifarre. Hanley & Belfus, Inc., Philadelphia (1997) pp 265–300.
(d) Sall D J, D L Bailey, J A Bastian, N Y Chirgadze, A C Clemens-Smith, M L Denney, M J Fisher, D D Geira, D S Gifford-Moore, R W Harper, L M Johnson, V J Klimkowski, T J Kohn, H S Lin, J R McCowan, A D Palkowitz, M E Richett, G F Smith, D W Snyder, K Takeuchi, J E Toth, M Zang. Diamino Benzo[b]thiophene Derivatives as a Novel Class of Active Site Directed Thrombin Inhibitors: 5. Potency, Efficacy and Pharmacokinetic Properties of Modified C-3 Side Chain Derivatives. J. Med. Chem., 43, 649–663 (2000).

The compounds of formula (I) exemplified herein have been found to exhibit a Kass of greater than $1 \times 10^6$ L/mole in the enzyme inhibition assay. For example, the compounds, or their pharmaceutically acceptable salts exemplified herein have been to exhibit Kass values of greater than $1 \times 10^6$ L/mole.

The ability of a test compound to elongate Partial Thromboplastin Time (Prothrombin Time) may be evaluated in the following test protocols.

Partial Thromboplastin Time (Prothrombin) Test Protocol
Venous blood is collected into 3.2% (0.109 M) trisodium citrate vacutainer tubes at 1 volume of anticoagulant to nine volumes of blood. The blood cells are separated by centrifugation at 700 g for ten minutes to yield plasma, which is frozen at 70° C. until required.

To perform the test, 100 µL of plasma are pipetted into in a glass test tube, 1 µL of test compound in DMSO is added, and allowed to warm to 37° over two minutes. 100 µL of warm (37°) Manchester (tissue thromboplastin) reagent (Helena Biosciences, UK) is added, allowed to equilibrate for two minutes. 100 µL of warm (37°) 25 mM calcium chloride solution is added to initiate clotting. The test tube is tilted three times through a 90° angle every five seconds to mix the reagents and the time to clot formation recorded. Data from a series of observations and test compound concentrations are analysed by a SAS statistical analysis program and a CT2 (Concentration required to double clotting time) for each compound is generated.

Compounds of the invention have been found to significantly elongate the partial thromboplastin time (Prothrombin time).

Alternative Prothrombin Time and APTT Protocols
Coagulation Determinations: Prothrombin Times and APTT values are determined in HUMAN PLASMA with a STA instrument (Stago). BioPT is a special non-plasma clotting assay triggered with human tissue factor (Innovin). Possible binding to albumen or to lipid are assessed by comparing the BioPT effects in the presence/absence of 30 mg/mL human albumen (HSA) and 1 mg/mL phosphatidyl choline (PC). Inhibitors are delivered in 50% aqueous methanol vehicle.

APTT ASSAY

75 µL plasma Citrol Baxter-Dade Citrated Normal Human Plasma
25 µL test solution
75 µL Actin Baxter-Dade Activated Cephaloplastin incubate 2 min min. @ 37° C.
75 µL $CaCl_2$ (0.02 M)

PT ASSAY

75 µL plasma
25 µL test solution
75 µL saline       incubate 1 min. @ 37° C.
75 µL Innovin Baxter-Dade Recombinant Human Tissue Factor

The invention claimed is:
1. A compound of formula (I)

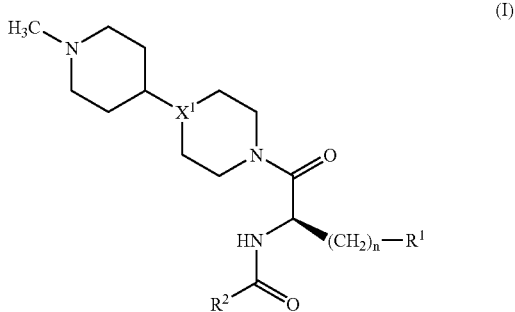

in which
$X^1$ represents N;
n is 1 or 2;

R¹ represents trifluoromethyl, COOH, CONH₂, SO₂NH₂, phenyl, pyridyl, C-linked imidazolyl (which may bear an N-(1–4C)alkyl substituent) or a (3–6C)cycloalkyl, oxa (4–6C)cycloalkyl, thia(4–6C)cycloalkyl or C-linked aza (4–6C)cycloalkyl group, which C-linked aza(4–6C)cycloalkyl group may bear an N-(1–4C)alkyl substituent; and R² is selected from

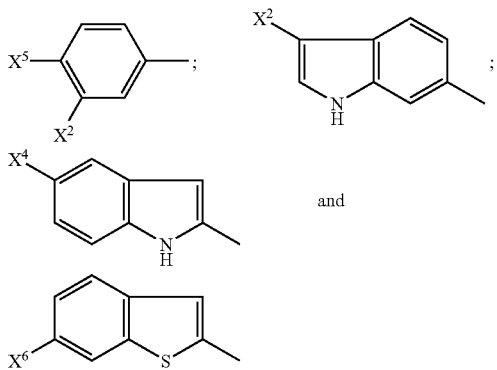

in which
X² represents a hydrogen atom, a halogen atom or an amino group;
X³ represents a hydrogen atom, a methyl group, a fluorine atom, a chlorine atom or a bromine atom;
X⁴ represents a hydrogen atom, a methyl, group or a halogen atom;
X⁵ represents a chlorine atom, a methoxy group or a methyl group; and
X⁶ represents a hydrogen atom, a halogen atom or a methyl group;
or a pharmaceutically acceptable metabolically labile ester thereof, or a pharmaceutically acceptable salt thereof.

2. A compound as claimed in claim 1, in which R¹ represents trifluoromethyl, COOH, CONH₂, phenyl, pyridyl, N-(1–4C)alkylimidazol-4-yl or a cyclopropyl, cyclohexyl, oxetanyl, tetrahydropyranyl, azetidinyl or piperidinyl group, which azetidinyl or piperidinyl group may bear an N-(1–4C)alkyl substituent.

3. A compound as claimed in claim 2, in which R¹ represents trifluoromethyl, COOH, CONH₂, phenyl, pyrid-2-yl, pyrid-3-yl, pyrid-4-yl, N-methylimidazol-4-yl, cyclopropyl, cyclohexyl, tetrahydropyran-4-yl or an N-methylpiperidin-4-yl group.

4. A compound as claimed in claim 1, in which X² represents a hydrogen atom or a halogen atom.

5. A compound as claimed in claim 4, in which
X² represents a hydrogen atom or a fluorine atom;
X³ represents a hydrogen atom, a fluorine atom, a chlorine atom or a methyl group;
X⁴ represents a chlorine atom;
X⁵ represents a chlorine atom or a methoxy group; and
X⁶ represents a chlorine atom.

6. A compound as claimed in claim 5, in which R² is 4-chlorophenyl, 4-methoxyphenyl, 3-fluoro-4-methoxyphenyl, indol-6-yl, 3-methylindol-6-yl, 3-chloroindol-6-yl, 5-fluoroindol-2-yl, 5-chloroindol-2-yl or 6-chlorobenzo[b]thiophen-2-yl.

7. A compound as claimed in claim 6, in which R² is 4-methoxyphenyl, indol-6-yl or 5-chloroindol-2-yl.

8. A compound as claimed in claim 1, in which
R¹ represents trifluoromethyl, COOH, CONH₂, phenyl, pyrid-2-yl, pyrid-3-yl, pyrid-4-yl, N-methylimidazol-4-yl, cyclopropyl, cyclohexyl, tetrahydropyran-4yl or an N-methylpiperidin-4-yl group; and
R² represents 4-chlorophenyl, 4-methoxyphenyl, 3-fluoro-4-methoxyphenyl, indol-6-yl, 3-methylindol-6-yl, 3-chloroindol-6-yl, 5-fluoroindol-2-yl, 5-chloroindol-2-yl or 6-chlorobenzo[b]thiophen-2 -yl.

9. A pharmaceutical composition, which comprises a compound as claimed in claim 1, together with a pharmaceutically acceptable diluent or carrier.

10. A process for preparing a compound as claimed in claim 1, which comprises
(a) reacting a compound of formula (II)

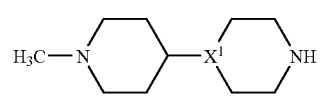

or a salt thereof, with a compound of formula (III)

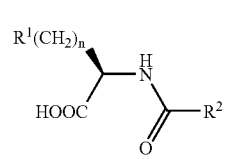

or a reactive derivative thereof; or
(b) reacting a compound of formula (IV)

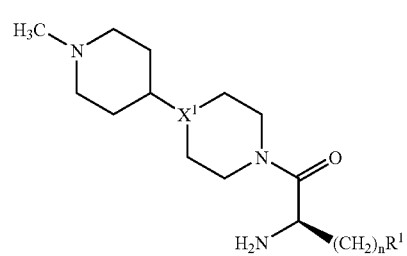

or a salt thereof, with a compound of formula (V)

or a reactive derivative thereof;
followed, if a pharmaceutically acceptable metabolically labile ester or a pharmaceutically acceptable salt is desired, by forming a pharmaceutically acceptable metabolically labile ester or salt.

11. A method of treating venous thrombosis, pulmonary embolism, arterial thrombosis, myocardial ischaemia, myocardial infarction or cerebral thrombosis in a subject requiring treatment, which comprises administering an effective amount of a compound as claimed in claim 1.

12. A pharmaceutical composition, which comprises a compound as claimed in claim 8, together with a pharmaceutically acceptable diluent or carrier.

13. A method of treating a venous thrombosis, pulmonary embolism, arterial thrombosis, myocardial ischaemia, myocardial infarction or cerebral thrombosis in a subject requiring treatment, which comprises administering an effective amount of a compound as claimed in claim 8.

14. A compound of formula (IV)
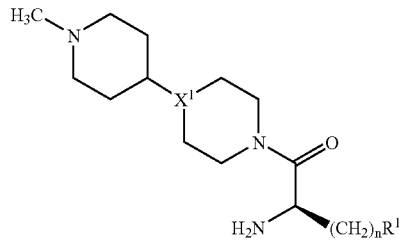
(IV)
or a salt thereof, in which
X¹ represents N;
n is 1 or 2; and
R¹ represents trifluoromethyl, COOH, CONH₂, SO₂NH₂, pyridyl, C-linked imidazolyl (which may bear an N-(1–4C)alkyl substituent) or a (3–6C)cycloalkyl, oxa(4–6C)cycloalkyl, thia(4–6C)cycloalkyl or C-linked aza(4–6C)cycloalkyl group, which C-linked aza(4–6C)cycloalkyl group may bear an N-(1–4C)alkyl substituent.
* * * * *